US009833205B2

(12) United States Patent
Sugie et al.

(10) Patent No.: US 9,833,205 B2
(45) Date of Patent: *Dec. 5, 2017

(54) X-RAY OUTPUT APPARATUS FOR REDUCTION OF SUPERFLUOUS RADIATION EXPOSURE

(71) Applicant: Sony Corporation, Tokyo (JP)

(72) Inventors: Yuki Sugie, Kanagawa (JP); Yoshinori Takagi, Kanagawa (JP); Hiromi Yoshinari, Kanagawa (JP); Hisakazu Shiraki, Kanagawa (JP)

(73) Assignee: Sony Corporation, Tokyo (JP)

( * ) Notice: Subject to any disclaimer, the term of this patent is extended or adjusted under 35 U.S.C. 154(b) by 337 days.

This patent is subject to a terminal disclaimer.

(21) Appl. No.: 14/422,776

(22) PCT Filed: Jun. 26, 2013

(86) PCT No.: PCT/JP2013/067525
§ 371 (c)(1),
(2) Date: Feb. 20, 2015

(87) PCT Pub. No.: WO2014/034244
PCT Pub. Date: Mar. 6, 2014

(65) Prior Publication Data
US 2015/0238152 A1 Aug. 27, 2015

(30) Foreign Application Priority Data

Aug. 27, 2012 (JP) .................................. 2012-186109
Mar. 13, 2013 (JP) .................................. 2013-050394

(51) Int. Cl.
*G01N 23/04* (2006.01)
*A61B 6/06* (2006.01)
(Continued)

(52) U.S. Cl.
CPC .............. *A61B 6/06* (2013.01); *A61B 6/4007* (2013.01); *A61B 6/4035* (2013.01); *G21K 1/04* (2013.01)

(58) Field of Classification Search
CPC ....... A61B 6/06; A61B 6/4007; A61B 6/4035; A61B 6/5241; A61B 6/08; G21K 1/04
(Continued)

(56) References Cited

U.S. PATENT DOCUMENTS 5,859,893 A      1/1999  Moorman et al.
9,414,800 B2 *   8/2016  Takagi ................. A61B 6/5241
(Continued)

FOREIGN PATENT DOCUMENTS

JP    2005-261838 A     9/2005
JP    2005-342514 A    12/2005
(Continued)

*Primary Examiner* — Courtney Thomas
(74) *Attorney, Agent, or Firm* — Chip Law Group

(57) ABSTRACT

Provided is an X-ray output apparatus including an X-ray output unit including a plurality of X-ray sources and configured to output parallel X-ray beams, a shield on which positions that are capable of blocking the output parallel X-ray beams and positions that are capable of transmitting the parallel X-ray beams are variable, and a control unit configured to control the output of the parallel X-ray beams in the X-ray output unit and the positions through which the parallel X-ray beams are transmitted in the shield.

19 Claims, 15 Drawing Sheets

(51) Int. Cl.
*A61B 6/00* (2006.01)
*G21K 1/04* (2006.01)

(58) Field of Classification Search
USPC .................................................. 378/145–155
See application file for complete search history.

(56) References Cited

U.S. PATENT DOCUMENTS

| | | |
|---|---|---|
| 2008/0095298 A1* | 4/2008 | Shefsky ................. G01N 23/02 378/2 |
| 2009/0232272 A1 | 9/2009 | Tsujii et al. |
| 2010/0183117 A1 | 7/2010 | Tsumuraya et al. |
| 2011/0216884 A1 | 9/2011 | Tsujii et al. |
| 2012/0134465 A1 | 5/2012 | Lee et al. |

FOREIGN PATENT DOCUMENTS

| | | |
|---|---|---|
| JP | 2007-333509 A | 12/2007 |
| JP | 2009-219708 A | 10/2009 |
| JP | 2009-291504 A | 12/2009 |
| JP | 2010-115270 A | 5/2010 |
| JP | 2011-098233 A | 5/2011 |
| JP | 2012-110719 A | 6/2012 |
| WO | WO 2009/011422 A1 | 1/2009 |

* cited by examiner

X-RAY OUTPUT APPARATUS FOR REDUCTION OF SUPERFLUOUS RADIATION EXPOSURE

TECHNICAL FIELD

The present disclosure relates to an X-ray output apparatus.

BACKGROUND ART

For example, an X-ray imaging apparatus (or an X-ray imaging system) utilizing X-rays output from an X-ray source, and an apparatus (or a system) having a tomosynthesis function utilizing X-rays are widely used, for example, in the medical field. Here, depending on the imaging subject, such as a case in which a human is the subject to be exposed to X-rays, it is desirable to control the region where the subject is exposed to X-rays in order to prevent superfluous radiation exposure.

Under such a situation, techniques are being developed to control the X-ray radiation region of the subject. As a technique to control the X-ray radiation region of the subject, for example, a technique disclosed in Patent Literature 1 below can be given.

CITATION LIST

Patent Literature

Patent Literature 1: JP 2009-291504A

SUMMARY OF INVENTION

Technical Problem

X-rays has a property of being spread as the distance between an X-ray source outputting X-rays and a subject or a detector detecting the X-rays becomes longer. Accordingly, when the X-ray irradiation region is not controlled, X-rays output from the X-ray source toward a specific portion of the subject (for example, an X-ray inspection target region) are radiated also to other portions than the specific portion of the subject. Accordingly, the subject is highly possibly exposed to superfluous radiation.

Here, as a measure to prevent the subject from superfluous radiation exposure described above, for example, the design of a collimator can be devised or an X-ray mobile diaphragm mechanism such as shown in Patent Literature 1 can be provided so as to output parallel X-ray beams to suppress the spread of X-rays. By causing the parallel X-ray beams to be output as described above, it becomes possible to reduce X-rays that are radiated to the portions other than the specific portion of the subject.

However, even if the X-ray spread is suppressed by, for example, causing the parallel X-ray beams to be output as described above, it is difficult to eliminate the X-ray spread. Therefore, even if the X-ray spread is suppressed by causing the parallel X-ray beams to be output as described above, for example, the superfluous radiation exposure given to the subject is not always sufficiently reduced.

As another measure to prevent the above superfluous radiation exposure of the subject, the distance between the X-ray source and the subject or the detector detecting the X-rays can be made shorter. However, since the temperature of the X-ray source becomes extremely high at the time of outputting X-rays, it is difficult to make the distance between the X-ray source and the subject or the detector detecting the X-rays as short as to ignore the influence of the X-ray spread.

The present disclosure proposes a novel and improved X-ray output apparatus which enables the reduction of superfluous radiation exposure given to a subject.

Solution to Problem

According to the present disclosure, there is provided an X-ray output apparatus including an X-ray output unit including a plurality of X-ray sources and configured to output parallel X-ray beams, a shield on which positions that are capable of blocking the output parallel X-ray beams and positions that are capable of transmitting the parallel X-ray beams are variable, and a control unit configured to control the output of the parallel X-ray beams in the X-ray output unit and the positions through which the parallel X-ray beams are transmitted in the shield.

Advantageous Effects of Invention

According to the present disclosure, the superfluous radiation exposure given to the subject can be reduced.

DESCRIPTION OF EMBODIMENTS

Hereinafter, preferred embodiments of the present invention will be described in detail with reference to the appended drawings. Note that, in this specification and the drawings, elements that have substantially the same function and structure are denoted with the same reference signs, and repeated explanation is omitted.

Hereinafter, the description will be made in the following order.

1. Method of reducing radiation exposure according to the present embodiment
2. X-ray output apparatus according to the present embodiment
3. Program according to the present embodiment (Method of Reducing Radiation Exposure According to the Present Embodiment)

A method of reducing radiation exposure according to the present embodiment will be described while the configuration of an X-ray output apparatus according to the present embodiment is described as appropriate. Hereinafter, the method of reducing radiation exposure according to the present embodiment will be described by taking an example in which the above method is used in an X-ray inspection system according to the present embodiment including an X-ray output apparatus according to the present embodiment.

Figure 1:
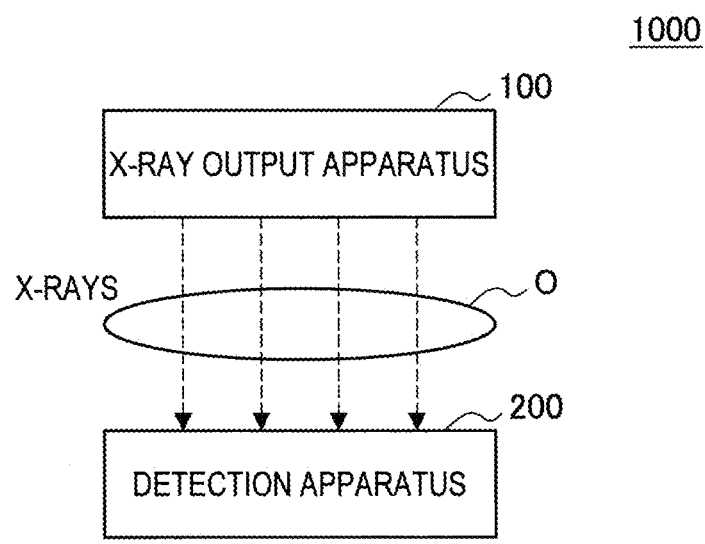
FIG. 1 is an illustration showing an example of a configuration of an X-ray inspection system according to the present embodiment including an X-ray output apparatus according to the present embodiment.

[1] Example of Configuration of X-Ray Inspection System According to the Present Embodiment FIG. 1 is an illustration showing an example of a configuration of an X-ray inspection system 1000 according to the present embodiment including an X-ray output apparatus 100 according to the present embodiment. The X-ray inspection system 1000 includes, for example, the X-ray output apparatus 100 and a detection apparatus 200. In the X-ray inspection system 1000, a subject O is inspected by the detection of X-rays in the detection apparatus 200, the X-rays being output from the X-ray output apparatus 100 and transmitted through the inside of the subject O.

The X-ray output apparatus 100 outputs parallel X-ray beams. An example of a configuration of the X-ray output apparatus 100 will be described later.

The detection apparatus 200 includes, for example, a detection unit (not shown) including a detector for detecting X-rays, and produces X-ray detection data by detecting the X-rays. Here, examples of the detector included in the detection apparatus 200 include an FPD (Flat Panel Detector, flat surface X-ray detector) and a photodiode. The X-ray detection data according to the present embodiment are, for example, data that are detected by the detector and exhibit the detection intensity of the X-rays having been transmitted through the subject Further, the detection apparatus 200 may include, for example, a processing unit (not shown) including an MPU (Micro Processing Unit) and various processing circuits, ROM (Read Only Memory, not shown), RAM (Random Access Memory, not shown), a communication unit (not shown), and the like.

The processing unit (not shown) included in the detection apparatus 200 converts produced X-ray detection data into projection data (two-dimensional projection data), for example, by two-dimensionally projecting the produced X-ray detection data as X-ray projection images. The processing unit (not shown) converts the X-ray detection data into the projection data, for example, by the Radon transform.

The ROM (not shown) included in the detection apparatus 200 stores a program used by the processing unit (not shown) included in the detection apparatus 200 and control data such as operation parameters. The RAM (not shown) included in the detection apparatus 200 temporarily stores a program executed by the processing unit (not shown) included in the detection apparatus 200, for example.

The communication unit (not shown) included in the detection apparatus 200 is a communication means included in the detection apparatus 200, and plays a role of communicating, with or without wires, with an external apparatus such as an image processing apparatus that processes the X-ray detection data or the projection data via a network (or directly).

Here, examples of the communication unit (not shown) included in the detection apparatus 200 include a communication antenna and an RF (Radio Frequency) circuit (wireless communication), an IEEE 802.15.1 port and a transmitting and receiving circuit (wireless communication), an IEEE 802.11b port and a transmitting and receiving circuit (wireless communication), and a LAN (Local Area Network) terminal and a transmitting and receiving circuit (wired communication). The communication unit (not shown) included in the detection apparatus 200 includes, for example, a configuration compatible with any standard capable of performing communication, such as a USB (Universal Serial Bus) terminal and a transmitting and receiving circuit, and any configuration communicable with an external apparatus via a network. A network according to the present embodiment includes, for example, a wired network such as LAN and WAN (Wide Area Network), a wireless network such as WLAN (Wireless Local Area Network) and WWAN (Wireless Wide Area Network) via a base station, or an internet using communication protocol such as TCP/IP (Transmission Control Protocol/Internet Protocol).

An example of the processing of the X-ray detection data or the projection data in the above image processing apparatus is processing in which an X-ray image based on the X-ray detection data is constituted by re-constituting three-dimensional data from the projection data which are converted from the X-ray detection data. Note that the processing of the X-ray detection data or the projection data in the image processing apparatus according to the present embodiment is not restricted to the above. Examples of the processing of the X-ray detection data or the projection data in the image processing apparatus according to the present embodiment include stitching processing (superposing processing) in which images are superposed for completing one image from results of imaging for plural times, offset processing for correcting fluctuation in X-ray intensity in the output of an X-ray source, and noise elimination processing for eliminating (or reducing) noises having fluctuation such as thermal noises and electric source noises.

Figure 2:
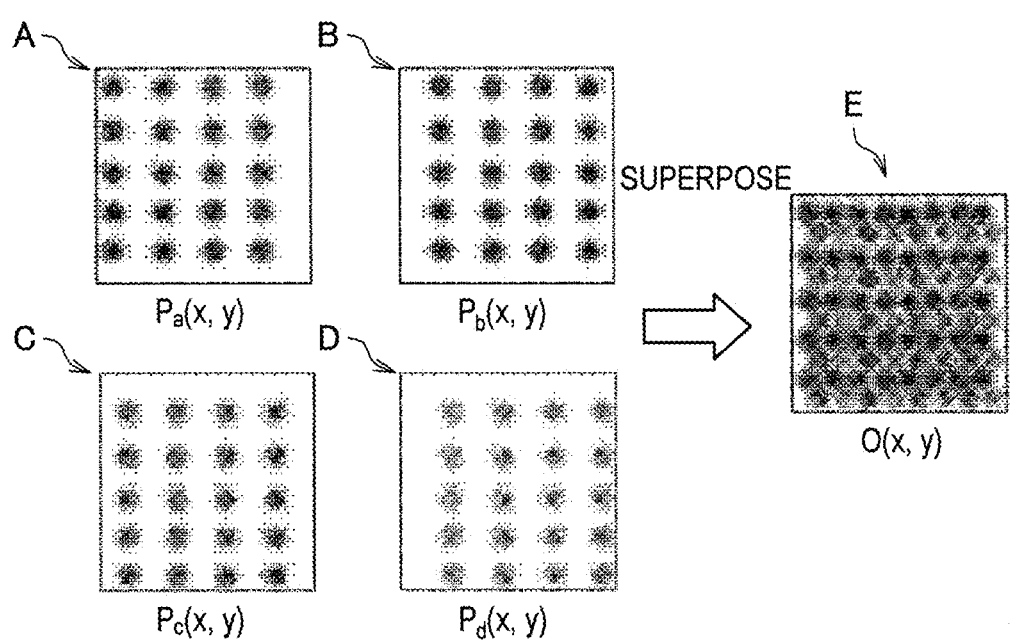
FIG. 2 is an illustration showing an example of processing of X-ray detection data in an image processing apparatus according to the present embodiment.

FIG. 2 is an illustration showing an example of processing of the X-ray detection data in the image processing apparatus according to the present embodiment, and shows an example of the stitching processing according to the present embodiment in the image processing apparatus according to the present embodiment. Here, A to D shown in FIG. 2 show, for example, examples of a plurality of X-ray images based on the X-ray detection data showing the respective detection results detected plural times in the detection apparatus 200 in a time-sharing manner. Further, E shown in FIG. 2 shows an example of the X-ray image (completed image) corresponding to the subject imaged by X-rays, the completed image being obtained by the stitching processing in the image processing apparatus according to the present embodiment.

The X-ray image (completed image) corresponding to the subject shown in E of FIG. 2 is obtained by, for example, superposing the plurality of the X-ray images based on the X-ray detection data showing the respective detection results detected plural times in the time-sharing manner, such shown in A to D of FIG. 2.

Here, as shown in FIG. 2, by superposing the plurality of the X-ray images based on the X-ray detection data showing the respective detection results detected plural times in the time-sharing manner, for example, it becomes possible to reduce mutual influences among the X-rays output from the X-ray source such as X-ray sources arranged side by side in an X-ray output unit (described later) included in the X-ray output apparatus 100. Further, as shown in FIG. 2, by superposing the plurality of the X-ray images based on the X-ray detection data showing the respective detection results detected plural times in the time-sharing manner, for example, it becomes possible to reduce the influence of the unevenness of the detected X-ray intensity, which may be generated by diffusion of X-rays.

Note that, in FIG. 2, although an example is shown in which the X-ray image (completed image) corresponding to the subject is obtained by superposing the four X-ray images shown in A to D of FIG. 2 by the image processing apparatus according to the present embodiment, the number of the X-ray images to be superposed by the image processing apparatus according to the present embodiment is not restricted to four. The image processing apparatus according to the present embodiment can obtain the X-ray image corresponding to the subject by superposing two or more X-ray images based on the X-ray detection data showing the respective detection results detected in the time-sharing manner, for example. More specifically, the image processing apparatus according to the present embodiment can obtain the X-ray image corresponding to the subject by superposing a plurality of X-ray images based on the X-ray detection data showing the respective detection results detected in the time-sharing manner, under various conditions such as the number of imaging times by the X-rays, the order of the imaging by the X-rays, and the position where the X-rays are output in the X-ray output unit (described later) included in the X-ray output apparatus 100.

The X-ray inspection system 1000 according to the present embodiment includes, for example, the configuration shown in FIG. 1. Note that the X-ray detection system according to the present embodiment is not restricted to the configuration shown in FIG. 1. For example, the X-ray detection system according to the present embodiment may further include the above described image processing apparatus.

[2] Summary of Method of Reducing Radiation Exposure According to the Present Embodiment Next, a summary of a method of reducing radiation exposure according to the present embodiment will be described. Hereinafter, the method of reducing radiation exposure according to the present embodiment will be described by taking an example in which the method of reducing radiation exposure according to the present embodiment is applied to the X-ray output apparatus 100 according to the present embodiment, the X-ray output apparatus 100 being included in the X-ray inspection system 1000 shown in FIG. 1.

Figure 3:
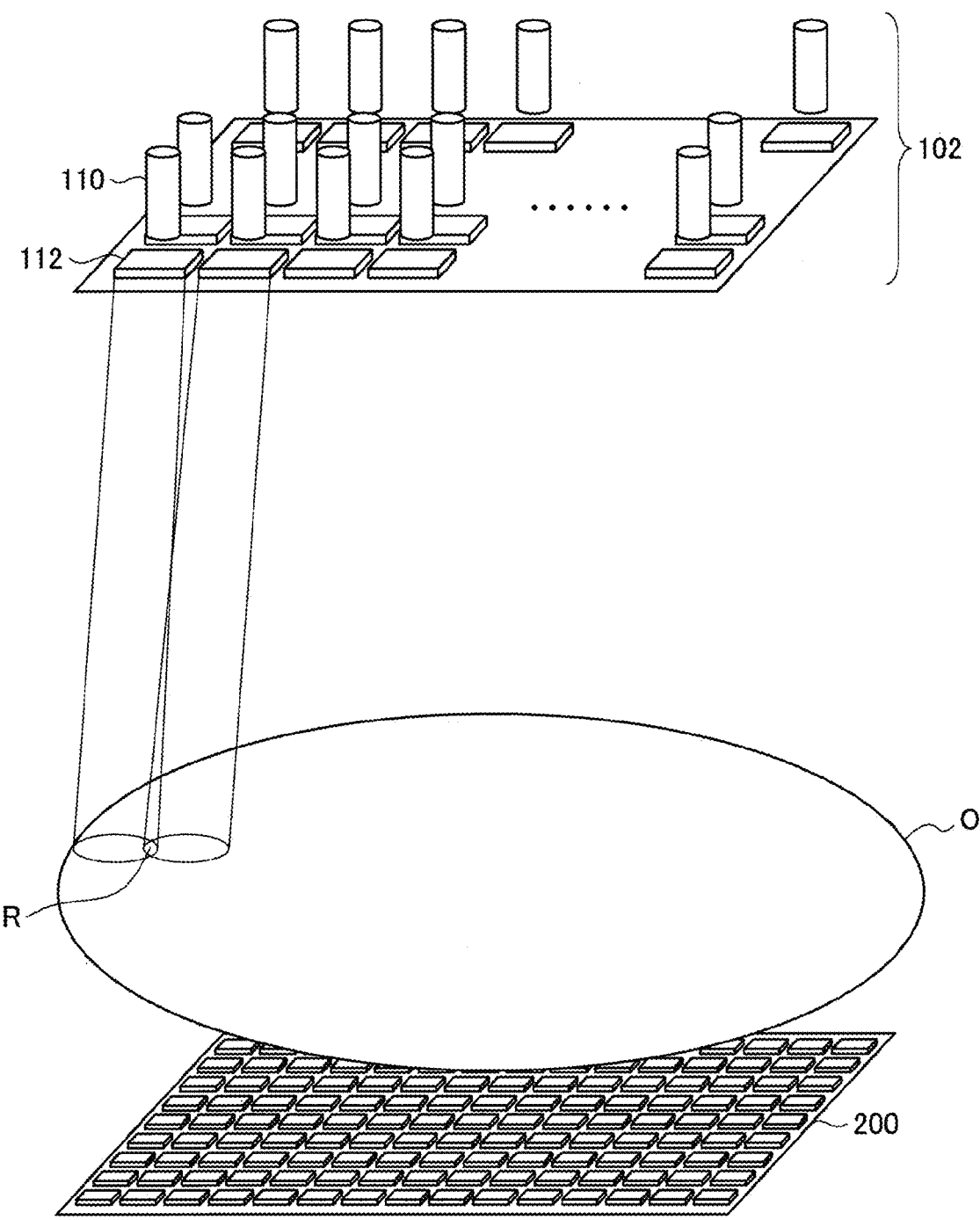
FIG. 3 is an illustration showing a method of reducing radiation exposure according to the present embodiment.

FIG. 3 is an illustration showing the method of reducing radiation exposure according to the present embodiment. FIG. 3 shows an example of an X-ray output unit 102 which is included in the X-ray output apparatus 100, the detection apparatus 200, and the subject O.

The X-ray output unit 102 includes a plurality of X-ray sources 110 and outputs parallel X-ray beams. The output of the parallel X-ray beams in the X-ray output unit 102 is controlled by, for example, a control unit (described later) initiatively performing processing in the method of reducing radiation exposure according to the present embodiment described later.

More specifically, the X-ray output unit 102 outputs the parallel X-ray beams by including, for example, the plurality of X-ray sources 110 including X-ray tubes which are electronic tubes for generating X-rays and a plurality of collimators 112 for forming the parallel X-ray beams from the X-rays generated by the X-ray tubes. FIG. 3 shows an example in which the X-ray output unit 102 is a planar radiation source including the X-ray sources 110 and collimators 112 arranged on a two-dimensional plane.

An example of the collimator 112 is a metal (for example, lead and iron) which is capable of blocking X-rays and has a slit portion capable of transmitting the X-rays. The collimator 112 is not restricted to the metal which has the slit portion capable of transmitting the X-rays, and may be formed by any structure and material which includes portions that block the X-rays and portions that transmit the X-rays to be able to form the parallel X-ray beams.

Note that the configuration of the X-ray output unit according to the present embodiment is not restricted to the configuration shown in FIG. 3. The X-ray output unit according to the present embodiment may include, for example, an X-ray source integrally constituted by the X-ray sources 110 and the collimators 112 so as to output the parallel X-ray beams. Further, although FIG. 3 shows the example of the X-ray sources 110 and the collimators 112 in a one-to-one relation, the X-ray sources 110 and the collimators 112 may not be in the one-to-one relation; for example, the plurality of X-ray sources 110 may correspond to the collimator 112.

The parallel X-ray beams output from the X-ray output unit 102 are transmitted through the subject O and are detected by the detector of the detection apparatus 200. Here, as described above, even if the X-ray spread is suppressed by outputting the parallel X-ray beams, it is difficult to eliminate the X-ray spread. Therefore, as shown in R of FIG. 3, a region may be generated which is irradiated with the parallel X-ray beams output from the plurality of X-ray sources 110 in an overlapping manner (hereinafter referred to as "overlap radiation region").

Figure 4:
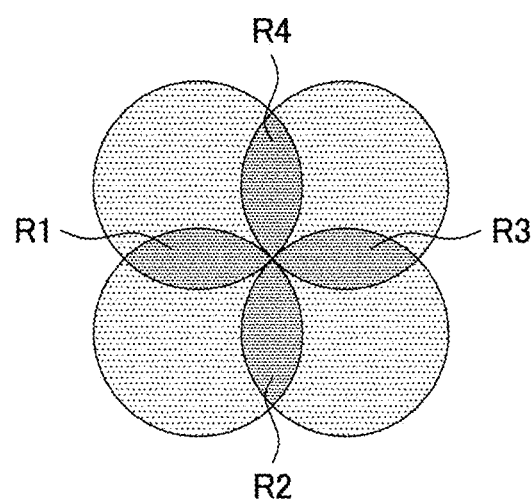
FIG. 4 is an illustration showing a method of reducing radiation exposure according to the present embodiment.

FIG. 4 is an illustration showing the method of reducing radiation exposure according to the present embodiment, and shows an example of the overlap radiation regions. FIG. 4 shows an example of overlap radiation regions R1 to R4 which may be formed by the parallel X-ray beams output from four X-ray sources 110.

As shown in R1 to R4 in FIG. 4, the parallel X-ray beams output from the plurality of X-ray sources 110 are radiated in an overlapping manner on the overlap radiation regions. The level of the radiation exposure in the overlap radiation regions R1 to R4 is higher than in the other regions to which the X-rays are radiated. Accordingly, the radiation exposure of the subject in the overlap radiation regions R1 to R4 is "invalid radiation exposure" which corresponds to superfluous radiation exposure of the subject.

Accordingly, the X-ray output apparatus 100 further includes, in addition to the X-ray output unit 102, a shield on which positions that can block the output parallel X-ray beams and positions that can transmit the parallel X-ray beams are variable. By controlling the output of the parallel X-ray beams in the X-ray output unit 102 and the positions through which the parallel X-ray beams are transmitted in the shield according to the present embodiment, the X-ray output apparatus 100 can reduce the invalid radiation exposure shown in R1 to R4 in FIG. 4 and reduce superfluous radiation exposure given to the subject.

Figure 5:
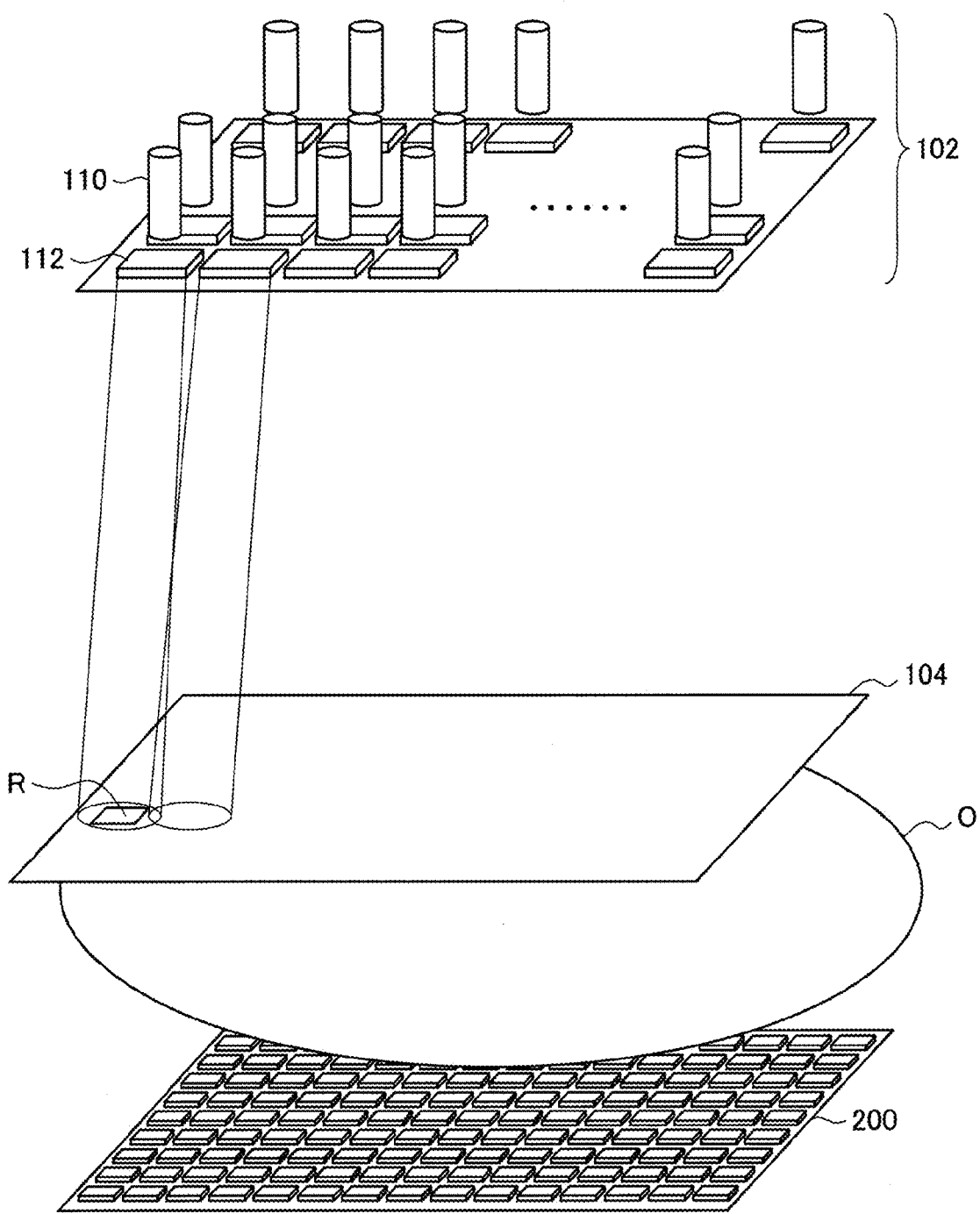
FIG. 5 is an illustration showing a method of reducing radiation exposure according to the present embodiment.

FIG. 5 is an illustration showing the method of reducing radiation exposure according to the present embodiment. FIG. 5 shows an example of the X-ray output unit 102 which is included in the X-ray output apparatus 100, a shield 104, the detection apparatus 200, and the subject O.

The shield 104 blocks the output parallel X-ray beams. Further, positions through which the parallel X-ray beams can be transmitted are variable in the shield unit 104. R shown in FIG. 5 shows an example of a region corresponding to the positions through which the parallel X-ray beams can be transmitted. Further, the positions through which the parallel X-ray beams are transmitted in the shield 104 are controlled by, for example, a control unit (described later) initiatively performing the processing in the method of reducing radiation exposure according to the present embodiment described later.

Examples of the shield 104 include a metal plate including a metal which can block the X-rays, such as lead and iron, glass containing the metal, and the like. The shield 104 may be formed of any material which can block the X-rays.

Figure 6:
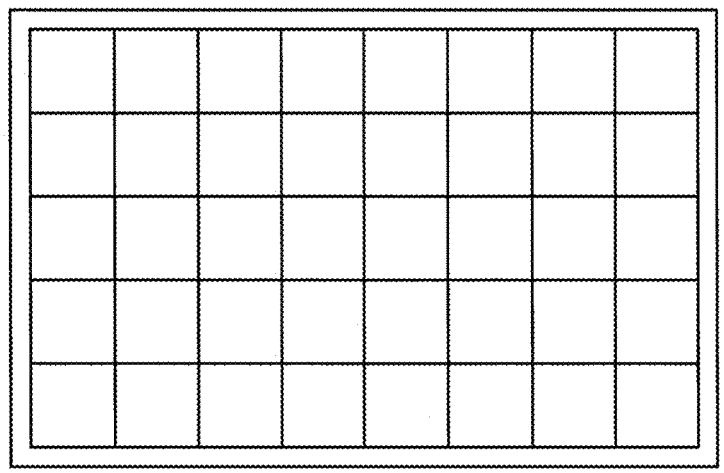
FIG. 6 is an illustration of an example of a shield included in an X-ray output apparatus according to the present embodiment.

FIG. 6 is an illustration showing an example of the shield 104 included in the X-ray output apparatus 100 according to the present embodiment.

As shown in FIG. 6, grid-shaped regions are set on the shield 104, for example.

Here, as the regions set on the shield, regions can be given which correspond to the collimators 112 included in the X-ray output unit 102 (including a case in which the X-ray sources 110 and the collimators 112 are integrally formed. The same holds true below.) in a one-to-one relation. Note that the regions set on the shield according to the present embodiment are not restricted to the above regions. For example, the region set on the shield according to the present embodiment may be regions corresponding to the plurality of collimators 112 included in the X-ray output unit 102.

Note that in a case in which the regions set on the shield according to the present embodiment are regions corresponding to the collimators 112 included in the X-ray output unit 102 in a one-to-one relation, it is possible to reduce more superfluous radiation exposure given to the subject than in a case in which the regions set on the shield according to the present embodiment are the regions corresponding to the plurality of collimators 112 included in the X-ray output unit 102. Hereinbelow, the method of reducing radiation exposure according to the present embodiment will be described by taking an example in which the regions set on the shield according to the present embodiment are regions corresponding to the collimators 112 included in the X-ray output unit 102 in a one-to-one relation.

Further, the positions through which the parallel X-ray beams are transmitted in the shield 104 are controlled by a control unit (described later) on the basis of the set regions.

Here, as the control of the positions through which the parallel X-ray beams are transmitted in the shield 104 by a control unit (described later), for example, a control can be given in which the parallel X-ray beams are not transmitted simultaneously in positions corresponding to regions that are adjacent to each other in the shield 104. Note that the control by a control unit (described later) according to the present embodiment is not restricted to the above. For example, a control unit (described later) according to the present embodiment can perform a control in which the parallel X-ray beams are allowed to be transmitted simultaneously in positions corresponding to adjacent regions in the shield, such as a control in which the parallel X-ray beams are not allowed to be transmitted simultaneously in positions corresponding to three or more successive regions in the shield.

Note that in a case in which a control unit (described later) according to the present embodiment performs control in which the parallel X-ray beams are not transmitted simultaneously in positions corresponding to adjacent regions in the shield, in the positions corresponding to regions that are adjacent to each other in the shield, it is possible to reduce more superfluous radiation exposure given to the subject than in a case in which control is performed in which the parallel X-ray beams are allowed to be transmitted simultaneously in positions corresponding to adjacent regions in the shield. Hereinbelow, the method of reducing radiation exposure according to the present embodiment will be described by taking an example in which a control unit (described later) according to the present embodiment performs control in which the parallel X-ray beams are not transmitted simultaneously in positions corresponding to adjacent regions in the shield.

For example, as described above, the grid-shaped regions are set on the shield 104, and the positions through which the parallel X-ray beams are transmitted in the shield 104 are controlled by a control unit (described later) on the basis of the set regions.

Here, as an example of the regions set on the shield 104 according to the present embodiment, a region that is set in advance on the shield 104 can be given. Note that the grid-shaped regions set on the shield 104 according to the present embodiment are not limited to the above. For example, the regions set on the shield 104 according to the present embodiment may be a region that is set virtually by a control unit (described later) initiatively performing processing according to the method of reducing radiation exposure according to the present embodiment. That is to say, in the X-ray output apparatus 100 according to the present embodiment, for example, the grid-shaped regions as shown in FIG. 6 may not be set on the shield 104 itself according to the present embodiment. Hereinbelow, the region that is set in advance on the shield 104 according to the present embodiment and the region that is set virtually on the shied 104 according to the present embodiment are collectively called "region set on the shield 104".

The region set on the shield 104 according to the present embodiment is not restricted to the rectangular grid regions as shown in FIG. 5. Examples of the regions set on the shield 104 according to the present embodiment include regions in various shapes, such as triangle grid regions, trapezoidal grid regions, pentagonal grid regions, and hexagonal grid regions. Note that specific examples of the regions set on the shield 104 according to the present embodiment will be described later.

Note that, in the shield 104, an example of a structure in which positions that can transmit the parallel X-ray beams are variable will be described in the processing in the method of reducing radiation exposure according to the present embodiment described later.

Referring again to FIG. 5, the parallel X-ray beams output from the X-ray output unit 102 are transmitted through the region R that can transmit X-rays in the shield 104 (one region is shown as the region R in FIG. 5, but a plurality of the regions R may be present) to be radiated on the subject O. Further, the parallel X-ray beams output from the X-ray output unit 102 are blocked by the shield 104 in a region other than the region R in the shield 104.

Figure 7:
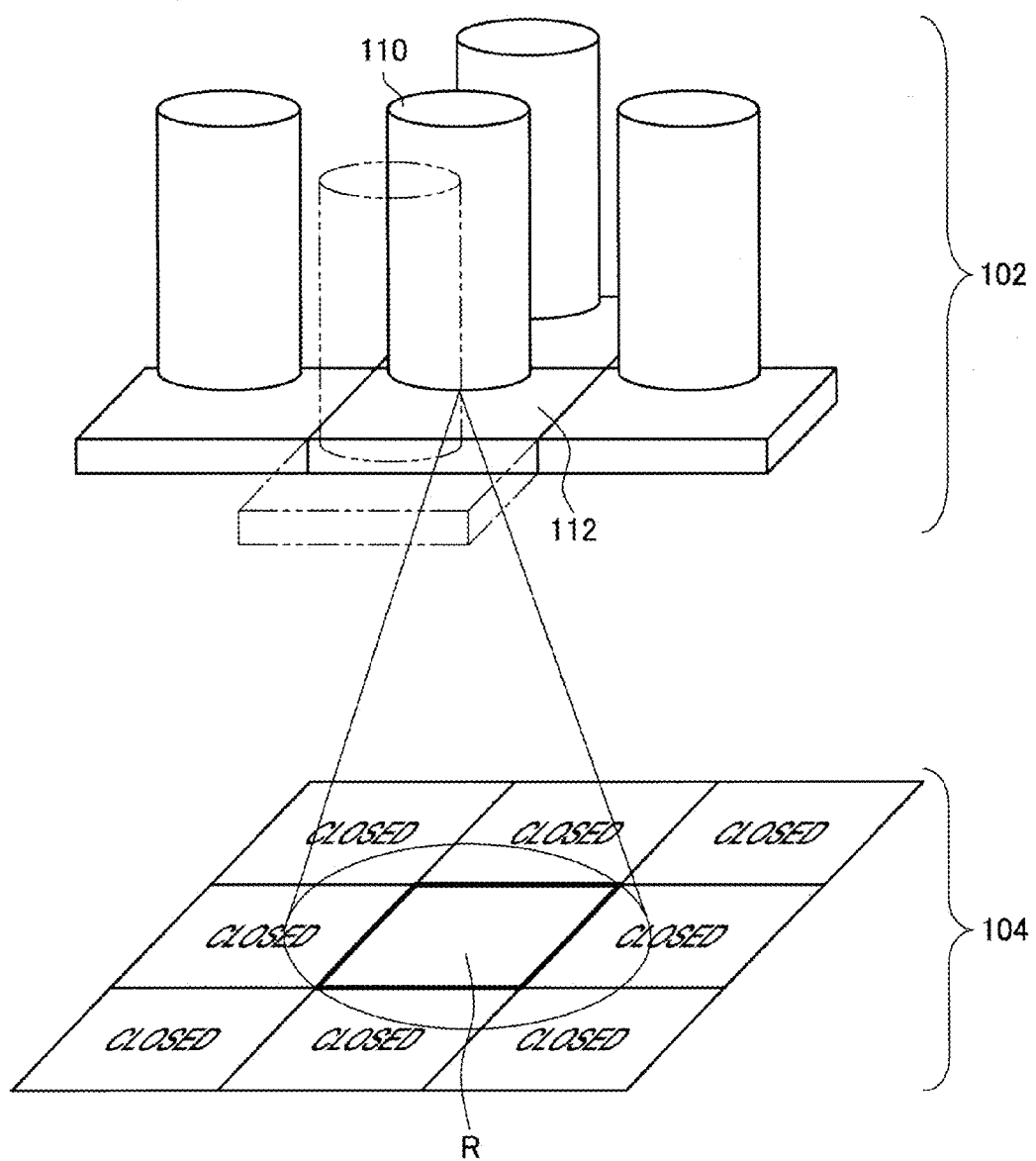
FIG. 7 is an illustration showing a purpose of a shield included in an X-ray output apparatus according to the present embodiment.

FIG. 7 is an illustration showing a purpose of the shield 104 included in the X-ray output apparatus 100 according to the present embodiment. In FIG. 7, a part of the X-ray output unit 102 included in the X-ray output apparatus 100 and a part of the shield 104 are shown as an example. In FIG. 7, further, regions that block X-rays in the shield 104 are shown as "closed". Note that in FIG. 7, the X-ray spread generated in the parallel X-ray beams is shown in an exaggerated manner.

As shown in FIG. 7, in the shield 104, for example, a region corresponding to the output parallel X-ray beams serves as the region R that can transmit X-rays, and in this region, the parallel X-ray beams are transmitted. Further, in a region adjacent to the region R in the shield 104, the shield 104 blocks X-rays.

Figure 8:
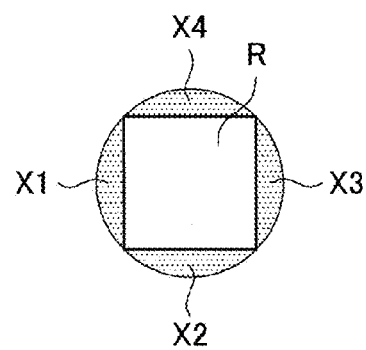
FIG. 8 is an illustration showing a purpose of a shield included in an X-ray output apparatus according to the present embodiment.

FIG. 8 is an illustration showing a purpose of the shield 104 included in the X-ray output apparatus 100 according to the present embodiment, and shows the region R in the shield 104 shown in FIG. 7.

As described above with reference to FIG. 3 and FIG. 4, in a case in which the shield 104 is not provided, invalid radiation exposure may be generated by the X-ray spread generated in the parallel X-ray beams. In contrast, as shown in FIG. 8 for example, by including the shield 104, the X-ray output apparatus 100 causes only the X-rays that are radiated to the region R to be transmitted through the shield 104 and does not allow the X-rays that are radiated to portions shown as X1 to X4 in FIG. 8 to be transmitted through the shield 104 (the X-rays are blocked by the shield 104) among the parallel X-ray beams output from the X-ray output unit 102.

By the X-ray output apparatus 100 including the shield 104 and controlling the output of the parallel X-ray beams in the X-ray output unit 102 and the positions through which the parallel X-ray beams are transmitted in the shield 104, the X-rays radiated to the portions shown as X1 to X4 in FIG. 8 are blocked by the shield 104 and are not radiated to the subject O. Accordingly, by the X-ray output apparatus 100 including the shield 104 and controlling the output of the parallel X-ray beams in the X-ray output unit 102 and the positions through which the parallel X-ray beams are transmitted in the shield 104, for example, it becomes possible to prevent the generation of the overlap radiation region, shown in FIG. 4, in the subject O, and to reduce invalid radiation exposure in the subject O.

Accordingly, by the X-ray output apparatus 100 performing the processing of controlling the output of the parallel X-ray beams in the X-ray output unit 102 and the positions through which the parallel X-ray beams are transmitted in the shield 104 as the processing in the method of reducing radiation exposure according to the present embodiment, it becomes possible to reduce superfluous radiation exposure given to the subject.

[3] Processing According to Method of Reducing Radiation Exposure According to the Present Embodiment Next, processing in the method of reducing radiation exposure according to the present embodiment in the X-ray output apparatus according to the present embodiment will be described. Hereinafter, the method of reducing radiation exposure according to the present embodiment will be described by taking an example in which the X-ray output apparatus according to the present embodiment is the X-ray output apparatus 100 included in the X-ray inspection system 1000 shown in FIG. 1.

As described above, the X-ray output apparatus 100 controls the output of the parallel X-ray beams in the X-ray output unit 102 and the positions through which the parallel X-ray beams are transmitted in the shield 104.

Figure 9:
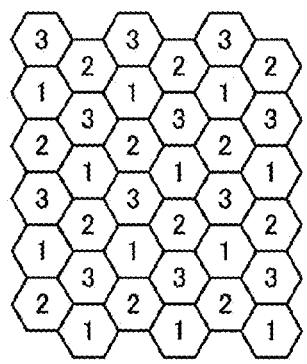
FIG. 9 is an illustration showing an example of controlling output of parallel X-ray beams in an X-ray output unit and positions through which parallel X-ray beams are transmitted in a shield in an X-ray output apparatus according to the present embodiment.
Figure 9:
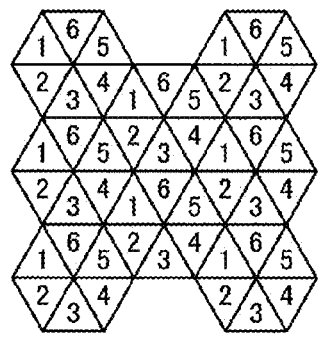

[3-1] Example of Processing According to Method of Reducing Radiation Exposure According to the Present Embodiment FIG. 9 is an illustration showing an example of controlling the output of the parallel X-ray beams in the X-ray output unit 102 and the positions through which the parallel X-ray beams are transmitted in shield 104 in the X-ray output apparatus 100 according to the present embodiment. Here, A to D shown in FIG. 9 each show an example of regions set on the shield 104. Further, "1" to "4" shown in A of FIG. 9, "1" to "3" shown in B of FIG. 9, "1" to "3" shown in C of FIGS. 9, and "1" to "6" shown in D of FIG. 9 indicate the order of positions through which X-ray output apparatus 100 causes the parallel X-ray beams to be transmitted.

(1) First example of processing according to method of reducing radiation exposure according to the present embodiment For example, as shown in A of FIG. 9, in a case in which rectangular grid regions are set, the X-ray output apparatus 100 causes the parallel X-ray beams to be selectively transmitted in the regions corresponding to the numbers in the order of "1" to "4" shown in A of FIG. 9.

More specifically, in a case in which the parallel X-ray beams are transmitted in regions corresponding to "1", the X-ray output apparatus 100 causes, for example, the X-ray sources 110 corresponding to at least the regions corresponding to "1" to output the parallel X-ray beams (an example of the control of the output of the parallel X-ray beams).

Here, the X-ray output apparatus 100 causes, for example, only the X-ray sources 110 corresponding to the regions corresponding to "1" to output the parallel X-ray beams, that is, causes the X-ray output section 104 to output the parallel X-ray beams only in the positions corresponding to the positions through which the parallel X-ray beams are transmitted in the shield 104. Note that the control of the output of the parallel X-ray beams in the X-ray output apparatus 100 is not restricted to the above. For example, X-ray output apparatus 100 may cause any number of X-ray sources 110 including the X-ray sources 110 corresponding to the regions corresponding to "1", such as all the X-ray sources 110 included in the X-ray output section 104, to output the parallel X-ray beams.

Further, in a case in which the parallel X-ray beams are transmitted in the regions corresponding to "1", the X-ray output apparatus 100, for example, sets the regions corresponding to "1" in the shield 104 as regions through which X-rays can be transmitted, and does not set the regions corresponding to "2" to "4" as the region through which X-rays can be transmitted (an example of the control of the positions through which the parallel X-ray beams are transmitted in the shield 104). Note that specific examples of a method of setting the regions through which X-rays can be transmitted in the X-ray output apparatus 100 (that is, a method of controlling the positions through which the parallel X-ray beams are transmitted in the shield 104) will be described later.

In a case in which the parallel X-ray beams are transmitted in the regions corresponding to "2", in a manner similar to that in the case of transmitting the parallel X-ray beams in the regions corresponding to "1", the X-ray output apparatus 100 causes, for example, the X-ray sources 110 corresponding to at least the regions corresponding to "2" to output the parallel X-ray beams (an example of the control of the output of the parallel X-ray beams). Further, in a case in which the parallel X-ray beams are transmitted in the regions corresponding to "2", in a manner similar to that in the case of transmitting the parallel X-ray beams in the regions corresponding to "1", the X-ray output apparatus 100 sets, for example, the regions corresponding to "2" in the shield 104 as the regions through which X-rays can be transmitted, and does not set the regions corresponding to "1", "3", and "4" as the regions through which X-rays can be transmitted (an example of the control of the positions through which the parallel X-ray beams are transmitted in the shield 104).

In a case in which the parallel X-ray beams are transmitted in the regions corresponding to "3", in a manner similar to that in the case of transmitting the parallel X-ray beams in the regions corresponding to "1", the X-ray output apparatus 100 causes, for example, the X-ray sources 110 corresponding to at least the regions corresponding to "3" to output the parallel X-ray beams (an example of the control of the output of the parallel X-ray beams). Further, in a case in which the parallel X-ray beams are transmitted in the regions corresponding to "3", in a manner similar to that in the case of transmitting the parallel X-ray beams in the regions corresponding to "1", the X-ray output apparatus 100 sets, for example, the regions corresponding to "3" in the shield 104 as the regions through which X-rays can be transmitted, and does not set the regions corresponding to "1", "2", and "4" as the regions through which X-rays can be transmitted (an example of the control of the positions through which the parallel X-ray beams are transmitted in the shield 104).

In a case in which the parallel X-ray beams are transmitted in the regions corresponding to "4", in a manner similar to that in the case of transmitting the parallel X-ray beams in the regions corresponding to "1", the X-ray output apparatus 100 causes, for example, the X-ray sources 110 corresponding to at least the regions corresponding to "4" to output the parallel X-ray beams (an example of the control of the output of the parallel X-ray beams). Further, in a case in which the parallel X-ray beams are transmitted in the regions corresponding to "4", in a manner similar to that in the case of transmitting the parallel X-ray beams in the regions corresponding to "1", the X-ray output apparatus 100 sets, for example, the regions corresponding to "4" in the shield 104 as the regions through which X-rays can be transmitted, and does not set the regions corresponding to "1" to "3" as the regions through which X-rays can be transmitted (an example of the control of the positions through which the parallel X-ray beams are transmitted in the shield 104).

For example, as shown in A of FIG. 9, in a case in which rectangular grid regions are set, the X-ray output apparatus 100 causes the parallel X-ray beams to be selectively transmitted in the regions corresponding to the numbers in the order of "1" to "4" shown in A of FIG. 9, as described above, for example.

Here, by causing the parallel X-ray beams to be selectively transmitted in the regions corresponding to the numbers in the order of "1" to "4" shown in A of FIG. 9, the X-ray output apparatus 100 can radiate the parallel X-ray beams output from the X-ray output section 104 to the entire specific portion (for example, an X-ray inspection target region) of the subject O. Accordingly, for example, in a case in which the rectangular grid regions are set as shown in A of FIG. 9, it becomes possible to obtain one complete X-ray image based on X-ray detection data by causing the parallel X-ray beams to be selectively transmitted in the regions corresponding to the numbers in the order of "1" to "4" shown in A of FIG. 9 and by detecting the parallel X-ray beams in the detection apparatus 200.

Further, by causing the parallel X-ray beams to be selectively transmitted in the regions corresponding to the numbers in the order of "1" to "4" shown in A of FIG. 9, in the positions corresponding to adjacent regions in the shield 104, the parallel X-ray beams are not transmitted simultaneously. Accordingly, since the generation of the overlap radiation region, as shown in FIG. 4, for example, can be prevented by causing the parallel X-ray beams to be selectively transmitted in the regions corresponding to the numbers in the order of "1" to "4" shown in A of FIG. 9, it becomes possible to reduce invalid radiation exposure in the subject O.

Accordingly, for example, in a case in which the rectangular grid regions are set as in A of FIG. 9, for example, by the X-ray output apparatus 100 controlling the output of the parallel X-ray beams in the X-ray output unit 102 and the positions through which the parallel X-ray beams are transmitted in the shield 104 as described above, it becomes possible to reduce superfluous radiation exposure given to the subject.

(2) Second Example of Processing According to Method of Reducing Radiation Exposure According to the Present Embodiment In a case in which rectangular grid regions are set as shown in B of FIG. 9, the X-ray output apparatus 100 causes the parallel X-ray beams to be selectively transmitted in the regions corresponding to the numbers in the order of "1" to "3" shown in B of FIG. 9, as in the case shown in A of FIG. 9, for example.

Here, by causing the parallel X-ray beams to be selectively transmitted in the regions corresponding to the numbers in the order of "1" to "3" shown in B of FIG. 9, the X-ray output apparatus 100 can radiate the parallel X-ray beams output from the X-ray output section 104 to the entire specific portion (for example, an X-ray inspection target region) of the subject O. Accordingly, for example, in a case in which the rectangular grid regions are set as shown in B of FIG. 9, it becomes possible to obtain one complete X-ray image based on X-ray detection data by causing the parallel X-ray beams to be selectively transmitted in the regions corresponding to the numbers in the order of "1" to "3" shown in B of FIG. 9 and by detecting the parallel X-ray beams in the detection apparatus 200. Further, for example, in a case in which the rectangular grid regions are set as shown in B of FIG. 9, it becomes possible to obtain one complete X-ray image with a smaller number of processing than in the case shown in A of FIG. 9.

Further, by causing the parallel X-ray beams to be selectively transmitted in the regions corresponding to the numbers in the order of "1" to "3" shown in B of FIG. 9, as in the case shown in A of FIG. 9, in the positions corresponding to adjacent regions in the shield 104, the parallel X-ray beams are not transmitted simultaneously. Accordingly, as in the case shown in A of FIG. 9, since the generation of the overlap radiation region, as shown in FIG. 4, for example, can be prevented by causing the parallel X-ray beams to be selectively transmitted in the regions corresponding to the numbers in the order of "1" to "3" shown in B of FIG. 9, it becomes possible to reduce invalid radiation exposure in the subject O.

Accordingly, for example, in a case in which the rectangular grid regions are set as shown in B of FIG. 9, for example, by the X-ray output apparatus 100 controlling the output of the parallel X-ray beams in the X-ray output unit 102 and the positions through which the parallel X-ray beams are transmitted in the shield 104 as described above, it becomes possible to reduce superfluous radiation exposure given to the subject.

(3) Third Example of Processing According to Method of Reducing Radiation Exposure According to the Present Embodiment In a case in which hexagonal grid regions are set as shown in C of FIG. 9, the X-ray output apparatus 100 causes the parallel X-ray beams to be selectively transmitted in the regions corresponding to the numbers in the order of "1" to "3" shown in C of FIG. 9, as in the case shown in A of FIG. 9, for example.

Here, by causing the parallel X-ray beams to be selectively transmitted in the regions corresponding to the numbers in the order of "1" to "3" shown in C of FIG. 9, the X-ray output apparatus 100 can radiate the parallel X-ray beams output from the X-ray output section 104 to the entire specific portion (for example, an X-ray inspection target region) of the subject O. Accordingly, for example, in a case in which the hexagonal grid regions are set as shown in C of FIG. 9, it becomes possible to obtain one complete X-ray image based on X-ray detection data by causing the parallel X-ray beams to be selectively transmitted in the regions corresponding to the numbers in the order of "1" to "3" shown in C of FIG. 9 and by detecting the parallel X-ray beams in the detection apparatus 200. Further, for example, in a case in which the hexagonal grid regions are set as shown in C of FIG. 9, it becomes possible to obtain one complete X-ray image with a smaller number of processing than in the case shown in A of FIG. 9.

Further, by causing the parallel X-ray beams to be selectively transmitted in the regions corresponding to the numbers in the order of "1" to "3" shown in C of FIG. 9, as in the case shown in A of FIG. 9, in the positions corresponding to adjacent regions in the shield 104, the parallel X-ray beams are not transmitted simultaneously. Accordingly, as in the case shown in A of FIG. 9, since the generation of the overlap radiation region, as shown in FIG. 4, for example, can be prevented by causing the parallel X-ray beams to be selectively transmitted in the regions corresponding to the numbers in the order of "1" to "3" shown in C of FIG. 9, it becomes possible to reduce invalid radiation exposure in the subject O.

Accordingly, for example, in a case in which the hexagonal grid regions are set as in C of FIG. 9, for example, by the X-ray output apparatus 100 controlling the output of the parallel X-ray beams in the X-ray output unit 102 and the positions through which the parallel X-ray beams are transmitted in the shield 104 as described above, it becomes possible to reduce superfluous radiation exposure given to the subject.

(4) Fourth Example of Processing According to Method of Reducing Radiation Exposure According to the Present Embodiment In a case in which triangle grid regions are set as shown in D of FIG. 9, the X-ray output apparatus 100 causes the parallel X-ray beams to be selectively transmitted in the regions corresponding to the numbers in the order of "1" to "6" shown in C of FIG. 9, as in the case shown in A of FIG. 9, for example.

Here, by causing the parallel X-ray beams to be selectively transmitted in the regions corresponding to the numbers in the order of "1" to "6" shown in D of FIG. 9, the X-ray output apparatus 100 can radiate the parallel X-ray beams output from the X-ray output section 104 to the entire specific portion (for example, an X-ray inspection target region) of the subject O. Accordingly, for example, in a case in which the triangle grid regions are set as shown in D of FIG. 9, it becomes possible to obtain one complete X-ray image based on X-ray detection data by causing the parallel X-ray beams to be selectively transmitted in the regions corresponding to the numbers in the order of "1" to "6" shown in D of FIG. 9 and by detecting the parallel X-ray beams in the detection apparatus 200.

Further, by causing the parallel X-ray beams to be selectively transmitted in the regions corresponding to the numbers in the order of "1" to "6" shown in D of FIG. 9, as in the case shown in A of FIG. 9, in the positions corresponding to adjacent regions in the shield 104, the parallel X-ray beams are not transmitted simultaneously. Accordingly, as in the case shown in A of FIG. 9, since the generation of the overlap radiation region, as shown in FIG. 4, for example, can be prevented by causing the parallel X-ray beams to be selectively transmitted in the regions corresponding to the numbers in the order of "1" to "6" shown in D of FIG. 9, it becomes possible to reduce invalid radiation exposure in the subject O.

Accordingly, for example, in a case in which the triangle grid regions are set as in D of FIG. 9, for example, by the X-ray output apparatus 100 controlling the output of the parallel X-ray beams in the X-ray output unit 102 and the positions through which the parallel X-ray beams are transmitted in the shield 104 as described above, it becomes possible to reduce superfluous radiation exposure given to the subject.

By performing the processing according to the first example to the processing according to the fourth example, for example, the X-ray output apparatus 100 controls the output of the parallel X-ray beams in the X-ray output unit 102 and the positions through which the parallel X-ray beams are transmitted in the shield 104.

Note that in the X-ray output apparatus according to the present embodiment, the processing of controlling the output of the parallel X-ray beams in the X-ray output unit 102 and the positions through which the parallel X-ray beams are transmitted in the shield 104 is not restricted to the processing according to the first example to the processing according to the fourth example.

For example, in the processing according to the first example to the processing according to the fourth example, as shown in FIG. 9, in the positions corresponding to adjacent regions in the shield 104, the parallel X-ray beams are not transmitted simultaneously. However, as described above, the X-ray output apparatus according to the present embodiment can perform control in which the parallel X-ray beams are allowed to be transmitted simultaneously in the positions corresponding to adjacent regions in the shield.

Further, the shape and the number of the regions set on the shield 104 according to the present embodiment are not restricted to the examples shown in FIG. 9.

For example, the number of the regions set on the shield 104 varies depending on the size of the shield 104 and/or the size of the region set with respect to the shield 104.

Examples of the shape of the regions set on the shield 104 according to the present embodiment include regions having various shapes, such as trapezoidal regions and pentagonal grid regions.

Further, the shape of the regions set on the shield 104 according to the present embodiment is not restricted to the shape in which each side is constituted by a straight line as in the examples shown in FIG. 9, for example, and may be, for example, a shape in which at least a part is not a straight line.

Figure 10:
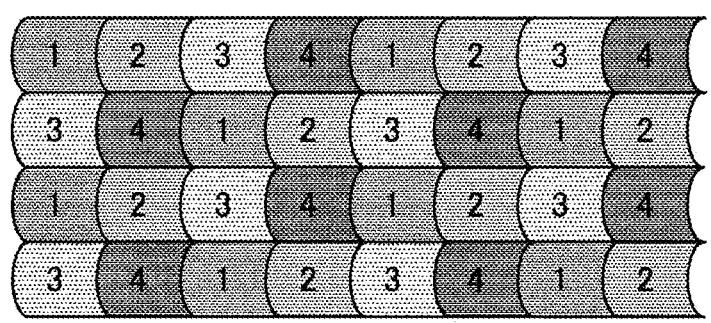
FIG. 10 is an illustration showing another example of a shape of a region that is set on a shield according to the present embodiment.
Figure 11:
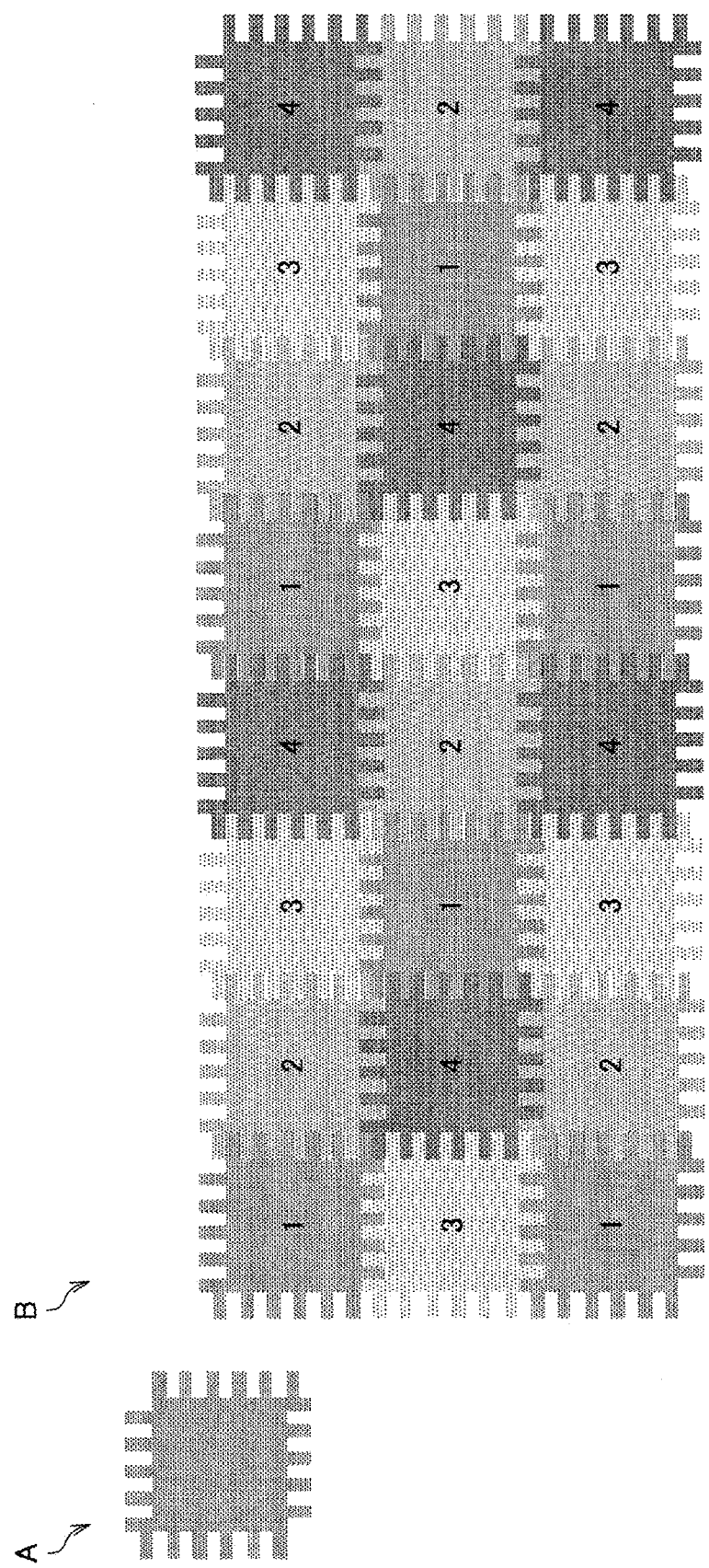
FIG. 11 is an illustration showing another example of a shape of a region that is set on a shield according to the present embodiment.

FIG. 10 to FIG. 13 are each an illustration showing another example of the shape of the regions that are set on the shield 104 according to the present embodiment. Here, "1" to "4" shown in FIGS. 10 and "1" to "4" shown in B of FIG. 11 show examples of the order of causing the parallel X-ray beams to be transmitted selectively.

The region set on the shield 104 may include, as shown in FIG. 10 for example, an arc shape in a part of the region.

The shape of the regions set on the shield 104 may be, for example, a shape including a convex and concave shape as shown in A of FIG. 11 or a shape including an uneven shape. In a case in which the shape of the regions set on the shield 104 is the convex and concave shape as shown in A of FIG. 11 or a shape including an uneven shape, for example, the shape of each region is set in a manner that the convex and concave shape or the uneven shape included in adjacent regions engage with each other as shown in B of FIG. 11, for example.

Note that in A shown in FIG. 11, an example in which the entire regions set on the shield 104 have convex and concave shapes is shown; however, the shape of the regions set on the shield 104 and the shape of the regions including convex and concave shapes are not limited to the example shown in A of FIG. 11. For example, the regions set on the shield 104 may partly have a convex and concave shape (this holds true for the case in which the shape of the regions set on the shield 104 includes an uneven shape).

Figure 12:
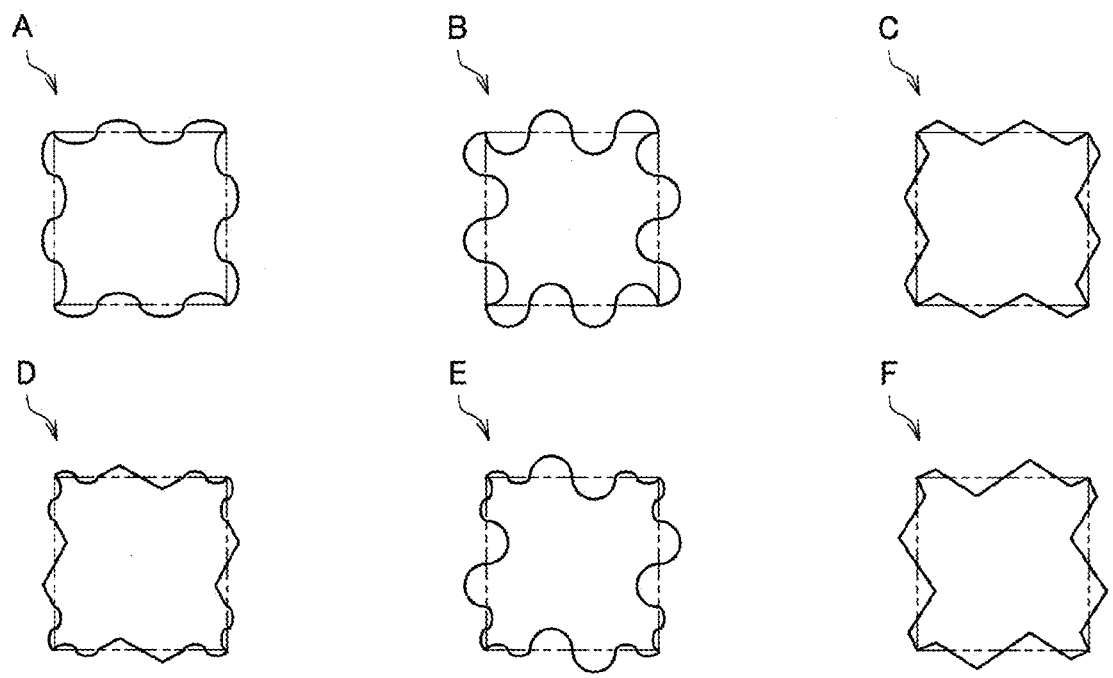
FIG. 12 is an illustration showing another example of a shape of a region that is set on a shield according to the present embodiment.

Alternatively, the shape of the regions set on the shield 104 may be a shape shown in A to F of FIG. 12, for example. Here, A and B shown in FIG. 12 show examples of a shape including a plurality of arc shapes, and C shown in FIG. 12 shows an example of a shape including a plurality of uneven shapes. Further, D shown in FIG. 12 shows an example of a shape including a plurality of arc shapes and a plurality of uneven shapes. E and F shown in FIG. 12 show examples of an asymmetric shape. Specifically, E shown in FIG. 12 shows, for example, an example of a shape to which asymmetry is further added to the shape of B shown in FIG. 12, and F shown in FIG. 12 shows an example of a shape to which asymmetry is further added to the shape of C shown in FIG. 12. The asymmetric shape according to the present embodiment refers to, for example, a shape in which two divided regions that are obtained by dividing the region along a straight line passing through the center of the region do not have symmetric shapes.

Here, as an asymmetric shape, the shape being set on the shield 104 according to the present embodiment, for example, in a case in which the rectangular shape shown in FIG. 6 is used as a reference, a shape is given in which asymmetry of the corner portion in the rectangular shape is made smaller and in which asymmetry of the center portion in the side of the rectangular shape is made larger.

Figure 13:
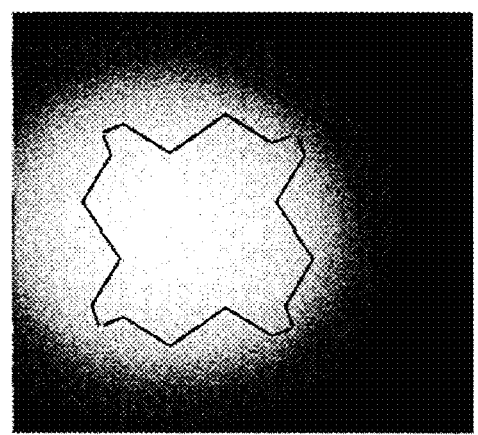
FIG. 13 is an illustration showing another example of a shape of a region that is set on a shield according to the present embodiment.

For example, as shown in FIG. 13, in X-ray irradiation, the ratio of scattered X-rays becomes larger as the distance the center of the X-ray source becomes larger.

Accordingly, by setting the asymmetric shape according to the present embodiment as a shape in which asymmetry of the corner portion in the rectangular shape is made smaller and in which asymmetry of the center portion in the side of the rectangular shape is made larger, as described above, for example, the detection apparatus 200 can generate X-ray detection data obtained by taking the influence of the scattered X-rays into account. Further, by setting the asymmetric shape according to the present embodiment as the above described shape related to asymmetry, for example, it becomes possible to obtain an entire image by using more stable X-ray radiation portions in the image processing apparatus according to the present embodiment that processes X-ray detection data or projection data. Note that, it is needless to say that the asymmetric shape set on the shield 104 according to the present embodiment is not restricted to the shape shown above as an example in which the rectangular shape shown in FIG. 6, for example, is used as a reference.

As described above, as the shape of the regions set on the shield 104 according to the present embodiment, for example, a shape having each side constituted by a straight line can be given, as in the example shown in FIG. 9, for example. Further, the shape of the regions set on the shield 104 according to the present embodiment may be a shape in which at least a part is not a straight line, as shown in FIG. 10 to FIG. 12, for example. As an example of the regions according to the present embodiment on which a shape in which at least a part is not a straight line is set, for example, a "region having an asymmetric shape" as shown in E and F of FIG. 12, and/or a "region having a shape in which a shape that is not a straight line in the region is one or more of the following: an arc shape, a convex and concave shape, and an uneven shape" as shown in FIG. 10, FIG. 11, and A to D of FIG. 12.

Here, as described above with reference to FIG. 2, for example, by superposing a plurality of X-ray images based on X-ray detection data showing each detection result obtained by plural times of detection in a time-sharing manner, the image processing apparatus according to the present embodiment can obtain an X-ray image corresponding to the subject (a completed image).

Accordingly, by a region having a shape in which each side is constituted by a straight line being set on the shield 104 as in the example shown in FIG. 9, for example, by X-rays being transmitted in the order shown in FIG. 9, for example, and by the image processing apparatus according to the present embodiment superposing a plurality of X-ray images based on X-ray detection data, it is possible to obtain an X-ray image corresponding to the subject (a completed image).

As described above, by a region having a shape in which each side is constituted by a straight line being set on the shield 104 as in the example shown in FIG. 9, for example, it becomes possible to obtain an X-ray image corresponding to the subject (a completed image) in the image processing apparatus according to the present embodiment. However, in a case in which a plurality of plurality of X-ray sources are included as in the X-ray output unit 102 of the X-ray output apparatus 100, for example, depending on variations of the X-ray sources (e.g., variations generated at the time of manufacture or variations generated ex post facto by heat or the like), scattering of X-rays output from the X-ray sources may differ largely.

Here, if the scattering of X-rays output from the X-ray sources differs largely as described above, for example, in a case in which the image processing apparatus according to the present embodiment superposes a plurality of X-ray images based on X-ray detection data as shown in FIG. 2, for example, a user viewing the image might possibly recognize a seam generated by the superposition.

In contrast, in a case in which regions in which at least a part is not a straight line are set on the shield 104, as in FIG. 10 to FIG. 12, for example, if the scattering of X-rays output from the X-ray sources differs largely, the seam of images generated by superposing a plurality of X-ray images in the image processing apparatus according to the present embodiment is less visible. Accordingly, by setting regions in which at least a part is not a straight line on the shield 104, as shown in FIG. 10 to FIG. 12, for example, it becomes possible to prevent the user from recognizing the seam of images generated by superposing a plurality of X-ray images as described above.

Further, for example, by setting the regions in which at least a part is not a straight line on the shield 104, as in FIG. 10 to FIG. 12, the accuracy of imaging is further increased. Accordingly, for example, by setting the regions in which at least a part is not a straight line on the shield 104, as in FIG. 10 to FIG. 12, it becomes possible to perform stitching processing by a relatively simple addition calculation without a complex blending calculation, for example, in the image processing apparatus according to the present embodiment that processes X-ray detection data or projection data. Accordingly, by setting the regions in which at least a part is not a straight line on the shield 104, as in FIG. 10 to FIG. 12, for example, it becomes possible to increase the real-time property of processing in the image processing apparatus according to the present embodiment and to reduce the memory amount of calculation in the image processing apparatus according to the present embodiment.

Furthermore, in a case in which regions in which at least a part is not a straight line are set on the shield 104 as in FIG. 10 to FIG. 12, for example, it becomes possible to reduce superfluous radiation exposure given to the subject as in the case in which the regions having a shape in which each side is constituted by a straight line as in the example shown in FIG. 9, for example, are set on the shield 104.

As the example of the shape of the regions set on the shield 104 according to the present embodiment, the example shown in FIG. 9 and the examples shown in FIG. 10 to FIG. 12 are given. Note that it is needless to say that the shape of the regions set on the shield 104 according to the present embodiment is not restricted to the example shown in FIG. 9 and the examples shown in FIG. 10 to FIG. 12.

[3-2] Method of Controlling Positions through which Parallel X-Ray Beams are Transmitted in Shield 104

Next, an example of a method of controlling positions through which the parallel X-ray beams are transmitted in the shield 104 (a method of setting regions through which X-rays can be transmitted according to the present embodiment) in the processing according to the method of reducing radiation exposure according to the present embodiment will be more specifically described. Hereinbelow, an example of a method of controlling the positions through which the parallel X-ray beams are transmitted in the shield 104 will be described by taking as an example a case in which the regions set on the shield 104 according to the present embodiment are rectangular regions.

(I) First Example of Method of Controlling Positions through which Parallel X-Ray Beams are Transmitted in Shield 104

The shield 104 included in the X-ray output apparatus 100 includes a shield member opening-closing mechanism for each region set on the shield 104. The shield member opening-closing mechanism causes the parallel X-ray beams to be selectively transmitted by opening and closing of shield members. Further, in the method of reducing radiation exposure according to the present embodiment, the X-ray output apparatus 100 controls the positions through which the parallel X-ray beams are transmitted by setting each shield member open-and-close mechanism to be in a state in which the shield members are open or a state in which the shield members are closed.

Figure 14:
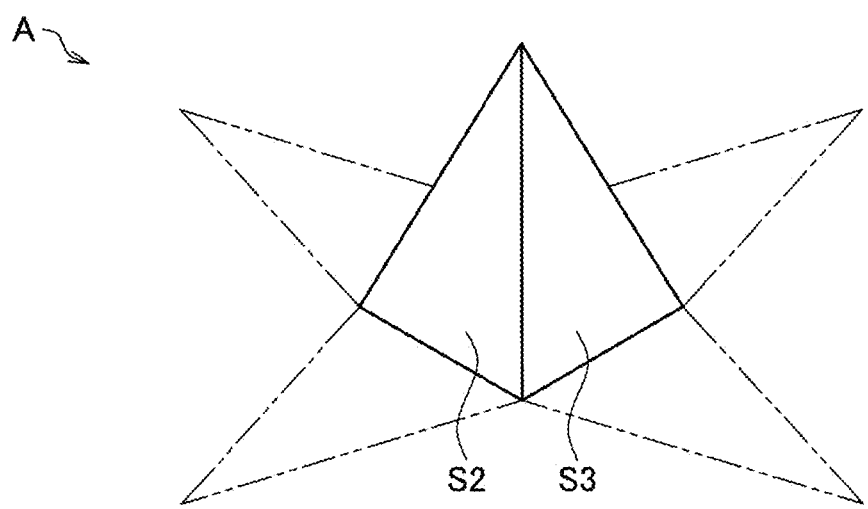
FIG. 14 is an illustration showing a first example of a method of setting a region through which X-rays can be transmitted according to the present embodiment in processing according to a method of reducing radiation exposure according to the present embodiment.
Figure 14:
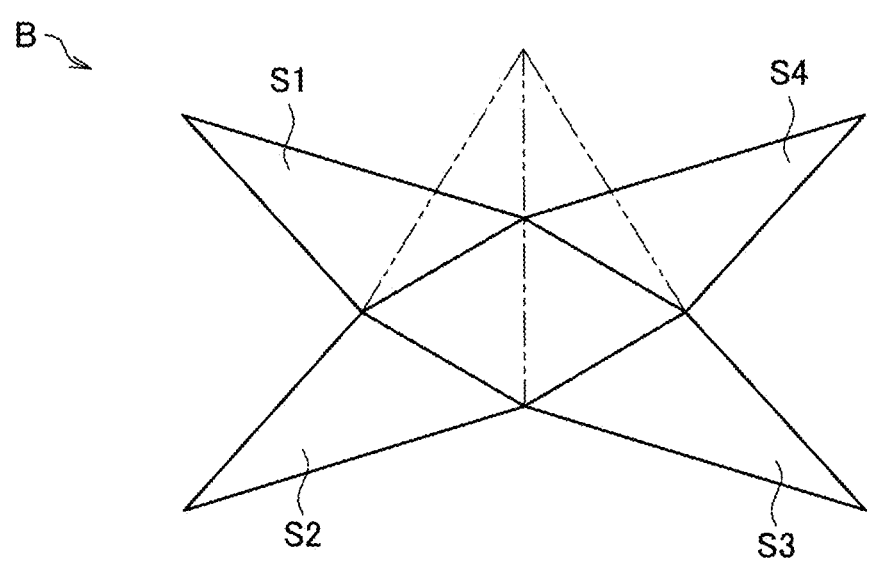

FIG. 14 is an illustration showing the first example of the method of setting a region through which X-rays can be transmitted according to the present embodiment in the processing according to the method of reducing radiation exposure according to the present embodiment. Here, FIG. 14 shows an example of the shield member opening-closing mechanism in a case in which the region set on the shield 104 is a rectangular region. Further, S1 to S4 shown in FIG. 14 each show an example of the shield member. Furthermore, A shown in FIG. 14 shows an example of the state in which the shield members are closed, and B shown in FIG. 14 shows an example in which the shield members are open.

For example, as shown in A of FIG. 14, by the shield members S1 to S4 being disposed to cover the corresponding region, the state in which the shield members are closed is achieved. Further, as shown in B of FIG. 14, by the shield members S1 to S4 being disposed not to cover the corresponding region, the state in which the shield members are open is achieved. Here, the shield member opening-closing mechanism as shown in FIG. 14 switches the state in which the shield members are open and the state in which the shield members are closed by the X-ray output apparatus 100 controlling the magnetic field generated by controlling current, for example.

Accordingly, by the X-ray output apparatus 100 controlling the positions through which the parallel X-ray beams are transmitted by setting each shield member opening-closing mechanism to be in the state in which the shield members are open and the state in which the shield members are closed, for example, as shown above with reference to A of FIG. 9, it becomes possible to cause the parallel X-ray beams to be selectively transmitted in the regions corresponding to the numbers in the order of "1" to "4" shown in A of FIG. 9.

Note that the shield member opening-closing mechanism according to the present embodiment is not restricted to the example shown in FIG. 14. For example, the shield member opening-closing mechanism according to the present embodiment may be any mechanism that can switch the state in which the shield members are open (the state in which X-rays are transmitted) and the state in which the shield members are closed (the state in which X-rays are blocked), such as a mechanism similar to a shutter in an imaging apparatus.

In the shield 104, in a case of changing the position of the shield member open-and-close mechanisms in a state in which the shield members are open as shown in B of FIG.

14, for example, the X-ray output apparatus 100 first sets all the shield member opening-closing mechanisms included in the shield 104 to be in a state in which the shield members are closed, as shown in A of FIG. 14, for example. Then, for example, the X-ray output apparatus 100 sets the shield member opening-closing mechanism corresponding to a specific position in the shield (e.g., the shield member opening-closing mechanism corresponding to the position through which the parallel X-ray beams are transmitted, as shown above with reference to FIG. 9) to be in a state in which the shield members are open as shown in B of FIG. 14, for example.

Here, as described above, for example, in a case in which, after all the shield member opening-closing mechanisms included in the shield 104 are set to be in a state in which the shield members are closed, the shield member opening-closing mechanism corresponding to the specific position is set to be in a state in which the shield members are open, the X-ray output apparatus 100 may cause the X-ray output unit 102 to keep outputting the parallel X-ray beams in the processing according to the method of reducing radiation exposure according to the present embodiment (an example of the control of the output of the parallel X-ray beams in the X-ray output unit 102), for example. In the above case, even when the X-ray output unit 102 is caused to keep outputting the parallel X-ray beams, after the X-ray output apparatus 100 sets a state in which the shield members are closed, the X-ray output apparatus 100 sets the shield member opening-closing mechanism corresponding to the specific position to be in a state in which the shield members are open. Accordingly, it becomes possible to prevent superfluous radiation exposure given to the subject.

Note that, as described above, for example, in a case in which all the shield member opening-closing mechanisms included in the shield 104 are set to be in a state in which the shield members are closed and then the shield member opening-closing mechanism corresponding to the specific position is set to be in a state in which the shield members are open, the control of the output of the parallel X-ray beams in the X-ray output unit 102 is not restricted to the above.

For example, in the processing according to the above method of reducing radiation exposure according to the present embodiment, the X-ray output apparatus 100 may cause the X-ray output unit 102 to output the parallel X-ray beams only to the position corresponding to the positions through which the parallel X-ray beams are transmitted in the shield 104. That is, the X-ray output apparatus 100 can control the output of the parallel X-ray beams in the X-ray output unit 102 in synchronization with the control of the shield member opening-closing mechanisms of the shield 104.

Further, in the shield 104, in a case of changing the position of the shield member opening-closing mechanisms in a state in which the shield members are open as shown in B of FIG. 14, for example, the X-ray output apparatus 100 may cause the X-ray output unit 102 to stop outputting the parallel X-ray beams until the change of the position of the shield member opening-closing mechanisms in a state in which the shield members are open is completed in the processing according to the method of reducing radiation exposure according to the present embodiment. As described above, by causing the X-ray output unit 102 to stop outputting the parallel X-ray beams until the change of the position of the shield member opening-closing mechanisms in a state in which the shield members are open is completed, it becomes possible to prevent superfluous radiation exposure given to the subject at the time when the position of the shield member opening-closing mechanisms in a state in which the shield members are open is changed.

Note that in a case in which the X-ray output unit 102 is caused to stop outputting the parallel X-ray beams until the change of the position of the shield member opening-closing mechanisms in a state in which the shield members are open is completed, the X-ray output apparatus 100 may not set the shield member opening-closing mechanism corresponding to the specific position to be in a state in which the shield members are open after all the shield member opening-closing mechanisms included in the shield 104 are set to be in a state in which the shield members are closed unlike in the above, for example. This is because it is possible to prevent superfluous radiation exposure given to the subject at the time when the position of the shield member opening-closing mechanisms in a state in which the shield members are open is changed, without setting a state in which the shield members are closed. More specifically, in a case in which the X-ray output unit 102 is caused to stop outputting the parallel X-ray beams until the change of the position of the shield member opening-closing mechanisms in a state in which the shield members are open is completed, the X-ray output apparatus 100 can change the position of the shield member opening-closing mechanisms in a state in which the shield members are open by any procedure such as "performing processing in which a region is changed from a state in which the shield members are open to a state in which the shield members are closed in parallel with processing in which a region is changed from a state in which the shield members are closed to a state in which the shield members are open", for example.

The X-ray output apparatus 100 controls the positions through which the parallel X-ray beams are transmitted by setting each shield member opening-closing mechanism to be in a state in which the shield members are open or a state in which the shield members are closed in the processing according to the method of reducing radiation exposure according to the present embodiment, as described above, for example. Note that the method of controlling the positions through which the parallel X-ray beams are transmitted in the shield 104 according to the present embodiment is not restricted to the controlling method according to the above first example.

(II) Second Example of Method of Controlling Positions through which Parallel X-Ray Beams are Transmitted in Shield 104

The shield 104 included in the X-ray output apparatus 100 includes transmission holes through which the parallel X-ray beams are transmitted, for example. Further, in the processing according to the method of reducing radiation exposure according to the present embodiment, the X-ray output apparatus 100 controls the positions through which the X-rays are transmitted by shifting the position of the transmission holes by moving the shield 104. Here, the X-ray output apparatus 100 moves the shield 104 in the horizontal direction, for example, by controlling a driving device having any configuration and using an electric motor, an air pressure, or an oil pressure, for example. Note that the shield 104 may be moved in various directions such as the vertical direction.

Here, the transmission holes according to the present embodiment correspond to the regions set on the shield 104. That is, as the shape of the transmission holes according to the present embodiment, the shape in which each side is constituted by a straight line as in the example shown in FIG. 9 is given, for example. Alternatively, the shape of the transmission holes according to the present embodiment may be a shape in which at least a part is not a straight line, as shown in FIG. 10 to FIG. 12, for example. Examples of the transmission holes according to the present embodiment having a shape in which at least a part is not a straight line include "transmission holes having an asymmetric shape" as shown in E and F of FIG. 12 and/or "transmission holes having a shape in which a portion that is not a straight line in the transmission holes is one or more of the following: an arc shape, a convex and concave shape, and an uneven shape" as shown in A to D of FIG. 10, FIG. 11, and FIG. 12. Note that it is needless to say that the shape of the transmission holes according to the present embodiment is not restricted to the example shown in FIG. 9 and the examples shown in FIG. 10 to FIG. 12.

Figure 15:
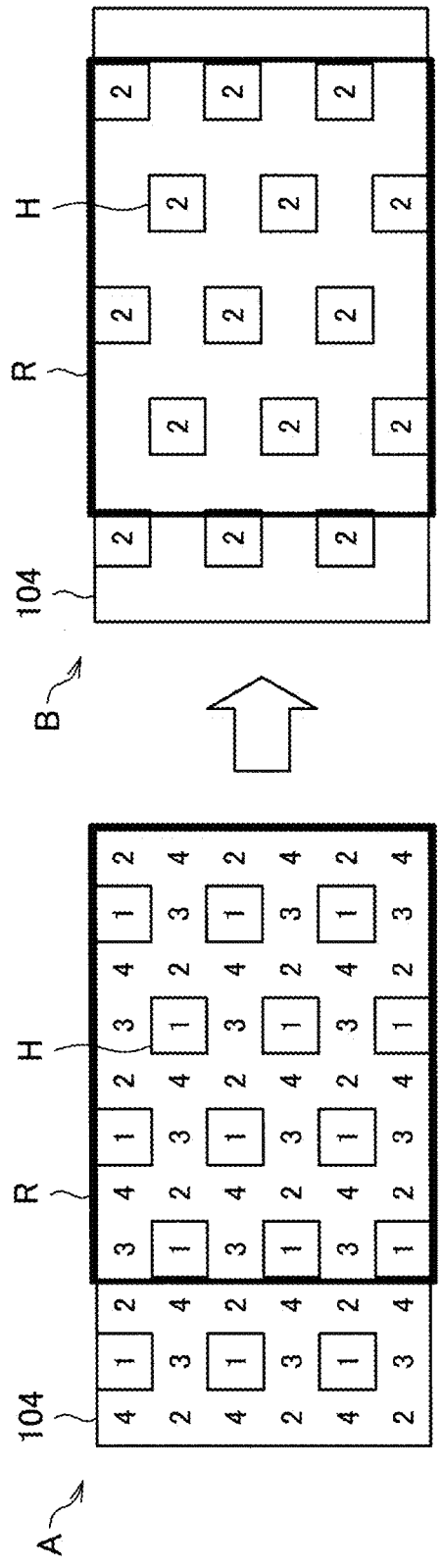
FIG. 15 is an illustration showing a second example of a method of setting a region through which X-rays can be transmitted according to the present embodiment in processing according to a method of reducing radiation exposure according to the present embodiment.
Figure 15:
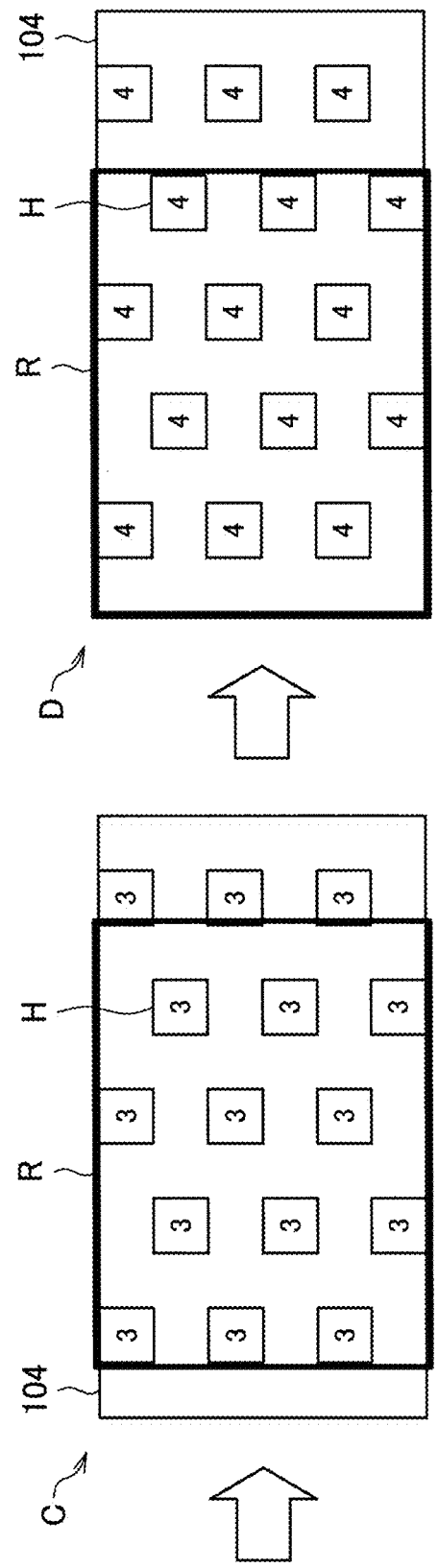

FIG. 15 is an illustration showing a second example of the method of setting the region through which X-rays can be transmitted according to the present embodiment in the processing according to a method of reducing radiation exposure according to the present embodiment. Here, FIG. 15 illustrates a case in which the regions set on the shield 104 are rectangular regions. R in FIG. 15 corresponds to a substantial shield portion in the shield 104 for protecting the subject from superfluous radiation exposure by blocking the parallel X-ray beams radiated to the subject. H shown in FIG. 15 shows a transmission hole, and in FIG. 15, in each of A to D in FIG. 15, only one transmission hole is denoted by the reference sign as a representative. Further, A, B, C, and D shown in FIG. 15 show the position of the shield 104, and the order of A , B, C, and D indicates the chronological order. Further, "1" to "4" shown in FIG. 15 show the order of positions at which the X-ray output apparatus 100 causes the parallel X-ray beams to be transmitted, as in FIG. 9.

In the processing according to the method of reducing radiation exposure according to the present embodiment, the X-ray output apparatus 100 controls the positions through which X-rays are transmitted by shifting the position of the transmission holes by moving the shield 104.

In a case in which the parallel X-ray beams are transmitted in the regions corresponding to "1", the X-ray output apparatus 100 moves the shield 104 in the horizontal direction, for example, so as to set the substantial shield portion R to be in a state shown in A of FIG. 15. In a case in which the substantial shield portion R is in a state shown in A of FIG. 15, the parallel X-ray beams output from the X-ray output unit 102 are transmitted through the regions corresponding to "1" and are not transmitted in the regions corresponding to "2" to "4".

In a case in which the parallel X-ray beams are transmitted in the regions corresponding to "2", the X-ray output apparatus 100 moves the shield 104 in the horizontal direction, for example, so as to set the substantial shield portion R to be in a state shown in B of FIG. 15. In a case in which the substantial shield portion R is in a state shown in B of FIG. 15, the parallel X-ray beams output from the X-ray output unit 102 are transmitted through the regions corresponding to "2" and are not transmitted in the regions corresponding to "1", "3", and "4".

In a case in which the parallel X-ray beams are transmitted in the regions corresponding to "3", the X-ray output apparatus 100 moves the shield 104 in the horizontal direction, for example, so as to set the substantial shield portion R to be in a state shown in C of FIG. 15. In a case in which the substantial shield portion R is in a state shown in C of FIG. 15, the parallel X-ray beams output from the X-ray output unit 102 are transmitted through the regions corresponding to "3" and are not transmitted in the regions corresponding to "1", "2", and "4".

In a case in which the parallel X-ray beams are transmitted in the regions corresponding to "4", the X-ray output apparatus 100 moves the shield 104 in the horizontal direction, for example, so as to set the substantial shield portion R to be in a state shown in D of FIG. 15. In a case in which the substantial shield portion R is in a state shown in D of FIG. 15, the parallel X-ray beams output from the X-ray output unit 102 are transmitted through the regions corresponding to "4" and are not transmitted in the regions corresponding to "1" to "3".

As described above, by the X-ray output apparatus 100 shifting the position of the transmission holes by moving the shield 104, it becomes possible to selectively transmit the parallel X-ray beams in the regions corresponding to the numbers in the order of "1" to "4" shown in FIG. 15.

For example, in a case in which the shield 104 is moved as shown in FIG. 15, the X-ray output apparatus 100 causes the X-ray output unit 104 to stop outputting the parallel X-ray beams, for example,. Further, after the movement of the shield 104 is completed, for example, the X-ray output apparatus 100 causes the X-ray output unit 102 to output the parallel X-ray beams (an example of the control of the output of the parallel X-ray beams in the X-ray output unit 102). As described above, by stopping the output of the parallel X-ray beams in the X-ray output unit 104 in a case in which the shield 104 is moved, it becomes possible to prevent superfluous radiation exposure given to the subject at the time when the shield 104 is moved, that is, when the position of the transmission holes is changed.

Further, in the processing according to the method of reducing radiation exposure according to the present embodiment, for example, the X-ray output apparatus 100 causes the X-ray output unit 102 to output the parallel X-ray beams only to the position corresponding to the positions through which parallel X-ray beams are transmitted in the shield 104 (an example of the control of the output of the parallel X-ray beams in the X-ray output unit 102). That is, the X-ray output apparatus 100 can control the output of the parallel X-ray beams in the X-ray output unit 102 in synchronization with the control of the movement of the shield 104.

Note that the control of the output of the parallel X-ray beams in the X-ray output apparatus 100 is not restricted to the above. For example, the X-ray output apparatus 100 may cause any number of the X-ray sources 110 including the X-ray sources 110 corresponding to the transmission holes (regions), such as all the X-ray sources 110 included in the X-ray output unit 104, to output the parallel X-ray beams.

(X-ray Output Apparatus According to the Present Embodiment)

Next, an example of a configuration of an X-ray output apparatus according to the present embodiment will be described which can perform the processing according to the method of reducing radiation exposure according to the present embodiment. An example of a configuration of the X-ray output apparatus of the present embodiment will be described by taking, as an example, a case in which the X-ray output apparatus according to the present embodiment is the X-ray output apparatus 100 included in the X-ray inspection system 1000 shown in FIG. 1.

Figure 16:
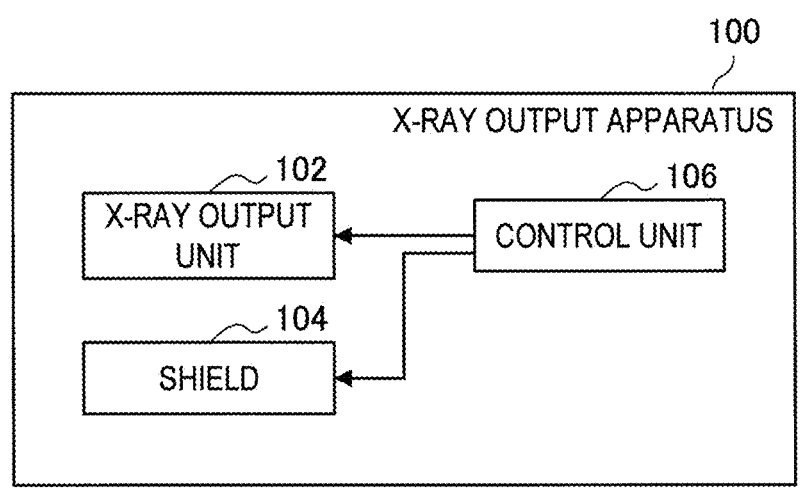
FIG. 16 is a block diagram showing an example of a configuration of an X-ray output apparatus according to the present embodiment.

FIG. 16 is a block diagram showing an example of a configuration of the X-ray output apparatus 100 according to the present embodiment. The X-ray output apparatus 100 includes, for example, an X-ray output unit 102, a shield 104, and a control unit 106.

The X-ray output apparatus 100 may include, for example, ROM (not shown) and RAM (not shown). For example, the X-ray output apparatus 100 connects the above structural elements through a bus as a transmission channel of data.

Here, the ROM (not shown) stores control data such as a program used in the control unit 106 and an operation parameter. The RAM (not shown) temporarily stores a program implemented by the control unit 106.

[Configuration Example of Hardware of X-Ray Output Apparatus 100]

Figure 17:
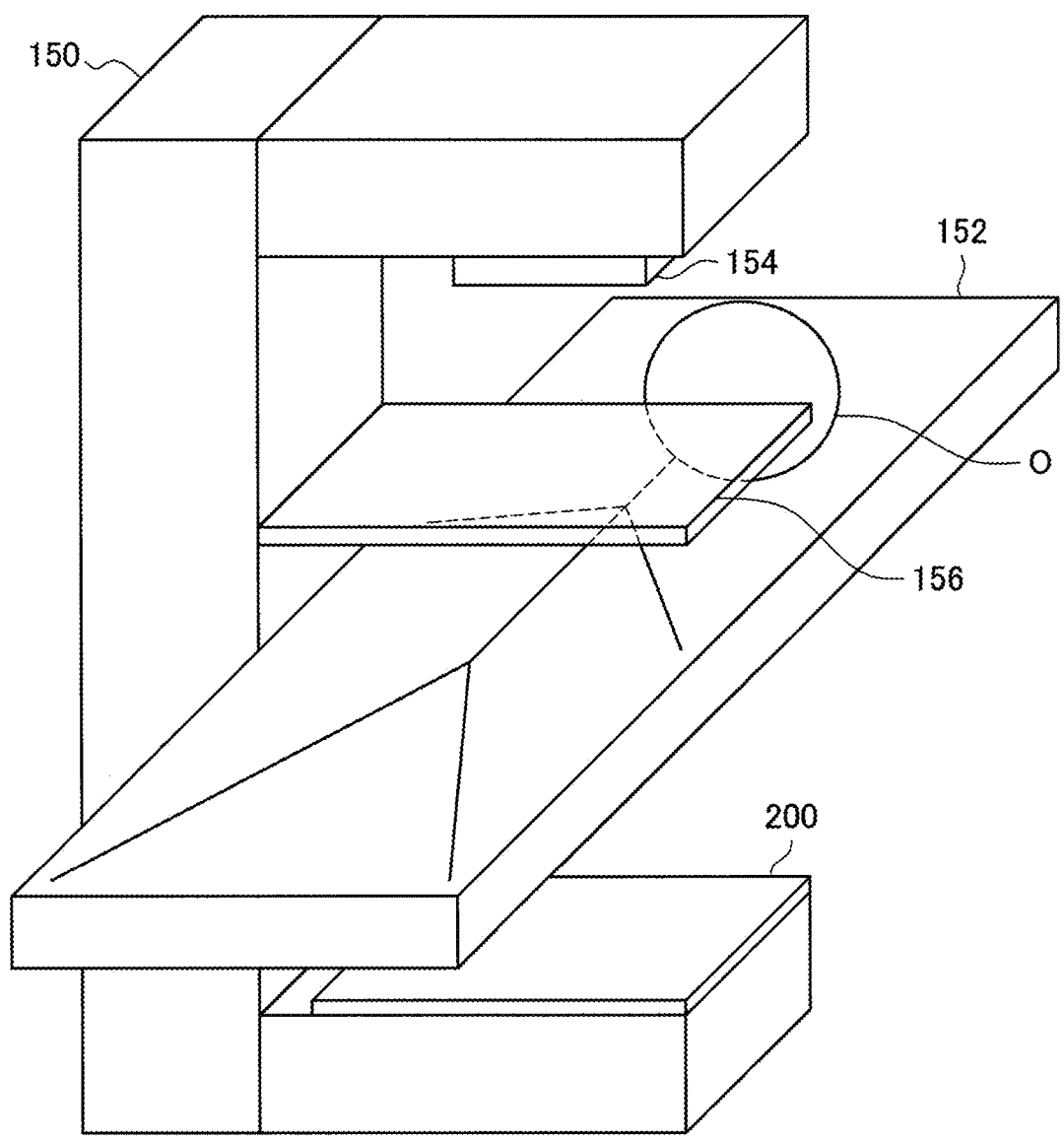
FIG. 17 is an illustration showing an example of a configuration of hardware of an X-ray output apparatus according to the present embodiment.

FIG. 17 is an illustration showing an example of a configuration of hardware of the X-ray output apparatus 100 according to the present embodiment. FIG. 17 additionally shows an example of the detection apparatus 200 such as FPD. FIG. 17 shows a human as an example of the subject O.

The X-ray output apparatus 100 includes, for example, an arm 150 holding each structural element, a subject imaging table 152, a multipoint parallel X-ray source 154, and a shield plate 156. Although not shown in FIG. 17, the X-ray output apparatus 100 includes, in the inside of the arm 150, for example, MPU (not shown) and various processing circuits functioning as the control unit 106 initiatively performing the processing according to the above described method of reducing radiation exposure according to the present embodiment. Further, the X-ray output apparatus 100 may include a driving device for switching the state of the shield member opening-closing mechanisms (e.g., a magnetic field generating device) and a driving device for moving the shield plate 156, for example.

The arm 150 holds the various structural elements of the X-ray output apparatus 100, and the detection apparatus 200. The subject imaging table 152 holds the subject O.

The multipoint parallel X-ray source 154 includes, for example, a plurality of X-ray tubes and a plurality of collimators, outputs the parallel X-ray beams, and functions as the X-ray output unit 102. The multipoint parallel X-ray source 154 generates X-rays with the X-ray tubes, forms the parallel X-ray beams from the above X-rays with the collimators, and outputs the parallel X-ray beams toward a bottom direction shown in FIG. 17.

The shield plate 156 is formed of a metal which can block the X-rays, such as lead and iron, and functions as the shield 104. For example, as shown in FIG. 17, the shield plate 156 having a role as the shield 104 is provided in the output direction of the parallel X-ray beams in the multipoint parallel X-ray source 154 having a role as the X-ray output unit 102, and between the multipoint parallel X-ray source 154 having a role as the X-ray output unit 102 and the subject O to which the parallel X-ray beams are radiated.

The X-ray output apparatus 100 performs the processing according to the method of reducing radiation exposure according to the present embodiment with the configuration shown in FIG. 17, for example. Note that the hardware configuration of the X-ray output apparatus 100 according to the present embodiment is not restricted to the configuration shown in FIG. 17.

For example, the X-ray output apparatus 100 and the detection apparatus 200 are described as separate apparatuses in the above description; however, the X-ray output apparatus 100 and the detection apparatus 200 may be a unit apparatus. In a case in which the X-ray output apparatus 100 and the detection apparatus 200 are a unit device, the detection apparatus 200 shown in FIG. 17 functions as, for example, a detecting unit that detects the parallel X-ray beams output from the X-ray output unit 102.

The X-ray output apparatus 100 may further include, for example, a communication device that performs communication with an external apparatus such as the image processing apparatus according to the present embodiment with or without wires. The above communication device has a role of a communication unit (not shown) in the X-ray output apparatus 100, for example. Examples of the communication device included in the X-ray output apparatus 100 include a communication antenna and an RF circuit (wireless communication), an IEEE 802.15.1 port and a transmitting and receiving circuit (wireless communication), and an IEEE 802.11b port and a transmitting and receiving circuit (wireless communication), and a LAN terminal and a transmitting and receiving circuit (wired communication). The communication device included in the X-ray output apparatus 100 may be any device compatible with any standard capable of performing communication, such as a USB terminal and a transmitting and receiving circuit, and any device communicable with an external apparatus via a network.

An example of the configuration of the X-ray output apparatus 100 will be described with reference to FIG. 16 again. As described above, the X-ray output unit 102 includes the plurality of X-ray sources 110 and outputs the parallel X-ray beams. Further, the output of the parallel X-ray beams in the X-ray output unit 102 is controlled by the control unit 106.

More specifically, in the X-ray source 110, X-rays are generated in the following manner. For example, in accordance with signals transferred from the control unit 106, current flows to a cathode filament of the X-ray tube included in the X-ray source 110 of the X-ray output unit 102, and thereby electrons collide with an anode target of the X-ray tube. In the X-ray sources 110, then, the collimators 112 of the X-ray output unit 102 forms the parallel X-ray beams from the generated X-rays.

The shield 104 blocks the output parallel X-ray beams. Further, in the shield 104, as described above, the positions through which the parallel X-ray beams can be transmitted varies by the state of the shield member open-and-close mechanisms being switched as shown in FIG. 14 or the position of the transmission holes being changed as shown in FIG. 15, for example.

More specifically, the positions through which the parallel X-ray beams are transmitted in the shield 104 is controlled by the control unit 106 as shown in the method of controlling the positions through which the parallel X-ray beams are transmitted in the shield 104 according to the first example shown in (I) above or the method of controlling the positions through which the parallel X-ray beams are transmitted in the shield 104 according to the second example shown in (II).

The control unit 106 has a role of initiatively performing the processing according to the method of reducing radiation exposure according to the present embodiment, and controls the output of the parallel X-ray beams in the X-ray output unit 102 and the positions through which the parallel X-ray beams are transmitted in the shield 104. The control unit 106 includes, for example, MPU and various processing circuits.

More specifically, for example, in a case in which the shield 104 includes the shield member opening-closing mechanisms as shown in FIG. 14, the control unit 106 controls the output of the parallel X-ray beams in the X-ray output unit 102 and the positions through which the parallel X-ray beams are transmitted in the shield 104 by using the method of controlling the positions through which the parallel X-ray beams are transmitted in the shield 104 according to the first example shown in (i) above.

Here, in a case in which the shield 104 includes the shield member opening-closing mechanisms as shown in FIG. 14, the X-ray output apparatus 100 includes a device for switching the state of the shield member opening-closing mechanisms (e.g., a magnetic field generation device), for example. The device for switching the state of the shield member opening-closing mechanisms may be a device included in the control unit 106 or a device separate from the control unit 106, for example.

Further, for example, in a case in which the shield 104 includes the transmission holes as shown in FIG. 15, the control unit 106 controls the output of the parallel X-ray beams in the X-ray output unit 102 and the positions through which the parallel X-ray beams are transmitted in the shield 104 by using the method of controlling the positions through which the parallel X-ray beams are transmitted in the shield 104 according to the second example shown in (II) above.

Here, in a case in which the shield 104 includes the transmission holes as shown in FIG. 15, the X-ray output apparatus 100 includes a driving device for moving the shield 104, for example. The driving device may be a device included in the control unit 106 or a device separate from the control unit 106, for example.

Note that the processing in the control unit 106 is not restricted to the above. For example, the control unit 106 may cause an apparatus which displays an image based on the X-ray detection data of the parallel X-ray beams having been transmitted through the shield 104 to perform display corresponding to the control of the output of the parallel X-ray beams in the X-ray output unit 102 and of the positions through which the parallel X-ray beams are transmitted in the shield 104 (the display corresponding to the processing according to the method of reducing radiation exposure according to the present embodiment). An example in which the apparatus that displays the image based on the X-ray detection data of the parallel X-ray beams having been transmitted through the shield 104 is the image processing apparatus according to the present embodiment will be described below.

More specifically, for example, the control unit 106 causes the communication unit (not shown) included in the X-ray output apparatus 100 or an external communication device to transmit display control information to the image processing apparatus according to the present embodiment. Here, an example of the display control information according to the present embodiment is information (data) that controls display corresponding to the "order of the positions through which the parallel X-ray beams are transmitted in the processing according to the method of reducing radiation exposure according to the present embodiment" as shown in FIG. 9 to FIG. 11 and FIG. 15.

The display control information according to the present embodiment includes, for example, information indicating the order of the positions through which the parallel X-ray beams are transmitted. Further, the display control information according to the present embodiment may include information indicating a display method. Examples of the display method according to the present embodiment include a "display method of displaying mixed colors that are assigned to each region corresponding to the order of the positions through which the parallel X-ray beams are transmitted", a "display method of displaying regions corresponding to the order of the positions through which the parallel X-ray beams are transmitted in a time-sharing manner according to the order", and the like.

The image processing apparatus according to the present embodiment having received the display control information according to the present embodiment displays, on a display screen, the display corresponding to the "control of the output of the parallel X-ray beams in the X-ray output apparatus 100 and the positions through which the parallel X-ray beams are transmitted" on the basis of the X-ray detection data (or projection data) transmitted from the detection apparatus 200 and the display control information according to the present embodiment, for example.

Figure 18:
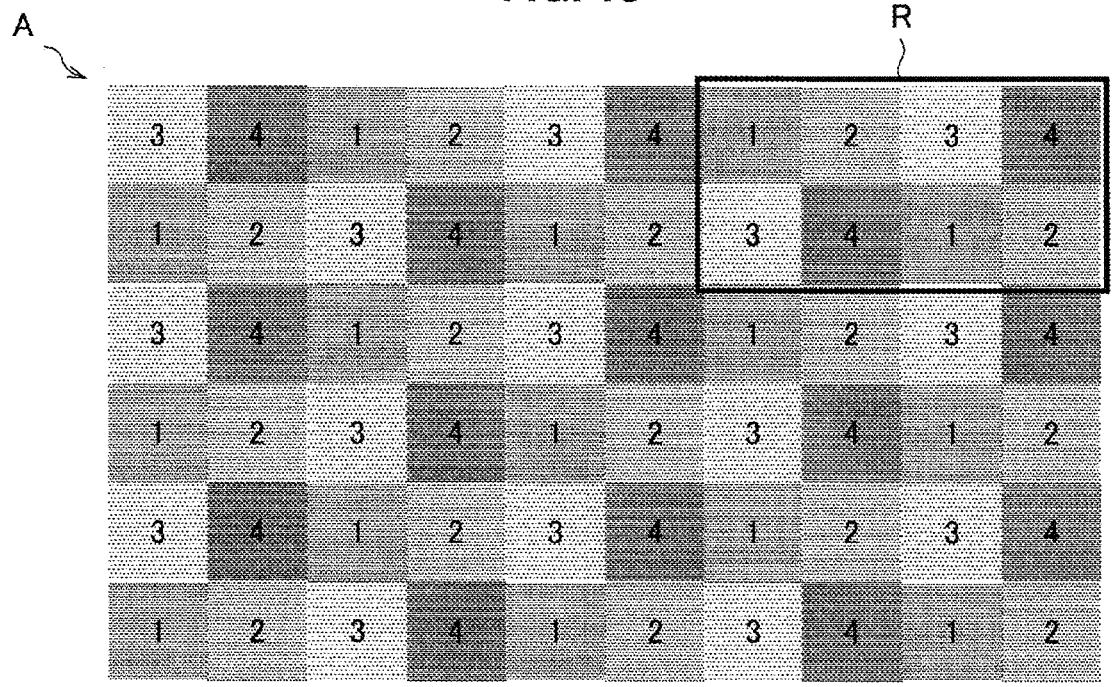
FIG. 18 is an illustration showing an example of processing in a control unit included in an X-ray output apparatus according to the present embodiment.
Figure 18:
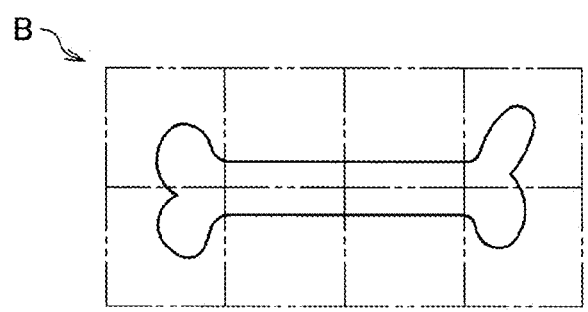
Figure 18:
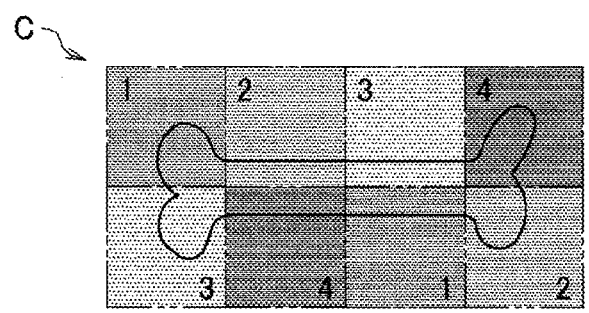

FIG. 18 is an illustration showing an example of processing in the control unit 106 included in the X-ray output apparatus 100 according to the present embodiment. A shown in FIG. 18 illustrates an example of the order of the positions through which the parallel X-ray beams are transmitted in the processing according to the method of reducing radiation exposure according to the present embodiment. Further, B and C shown in FIG. 18 each show an example of an image obtained by stitching X-day detection data by the parallel X-ray beams having been transmitted through a region R shown in A of FIG. 18.

Specifically, B shown in FIG. 18 shows an example of an image in a case in which display corresponding to the "control of the output of the parallel X-ray beams in the X-ray output apparatus 100 and the positions through which the parallel X-ray beams are transmitted" is not performed. Further, C shown in FIG. 18 shows an example of an image in a case in which display corresponding to the "control of the output of the parallel X-ray beams in the X-ray output apparatus 100 and the positions through which the parallel X-ray beams are transmitted" is performed. In the example shown in C of FIG. 18, colors assigned to each region corresponding to the order of positions through which the parallel X-ray beams are transmitted are mixed. Note that, as described above, the display method according to the present embodiment is not restricted to the mixing of colors assigned to each region corresponding to the order of positions through which the parallel X-ray beams are transmitted, as shown in C of FIG. 18.

For example, a user who views an X-ray image may want to modify the X-ray image. Here, when the user wants to modify the X-ray image, for example, in a case in which an image shown in B of FIG. 18 is displayed, the user may be unable to know the number of time of imaging from which the X-ray image that the user is viewing is obtained, whether or not the X-ray image that the user is viewing is an image obtained after stitching processing, and the like.

Accordingly, the X-ray output apparatus 100 (more specifically, the control unit 106, for example) causes the display control information according to the present embodiment to be transmitted to the image processing apparatus according to the present embodiment, for example. By the X-ray output apparatus 100 causing the display control information according to the present embodiment to be transmitted to the image processing apparatus according to the present embodiment, the image processing apparatus according to the present embodiment can display, on a display screen, an X-ray image in which colors assigned to each region corresponding to the order of the positions through which the parallel X-ray beams are transmitted are mixed, as shown in C of FIG. 18, for example. Further, a user who views the X-ray image in which colors assigned to each region corresponding to the order of the positions through which the parallel X-ray beams are transmitted are mixed, as shown in C of FIG. 18, for example, can know more easily the number of time of imaging from which the X-ray image that the user is viewing is obtained, whether or not the X-ray image that the user is viewing is an image obtained after stitching processing, and the like, for example.

Accordingly, by the X-ray output apparatus 100 causing the image processing apparatus according to the present embodiment to perform display corresponding to the control of the output of the parallel X-ray beams and of the positions through which the parallel X-ray beams are transmitted, for example, it is possible to increase the convenience of a user.

Further, as shown in FIG. 10 to FIG. 12, for example, in a case in which the shape of the regions set on the shield 106 includes a shape in which at least a part is not a straight line, the user is unlikely to recognize the boundary between the regions as compared to a case in which regions having a shape in which each side is constituted by a straight line as in the example shown in FIG. 9, for example, are set on the shield 104. Accordingly, as shown in FIG. 10 to FIG. 12, for example, in a case in which the shape of the regions set on the shield 106 includes a shape in which at least a part is not a straight line, effects of increasing the convenience of a user are further increased.

The X-ray output apparatus 100 performs the processing according to the reducing method according to the present embodiment by the configuration shown in FIG. 16, for example, and controls the output of the parallel X-ray beams in the X-ray output unit 102 and the positions through which the parallel X-ray beams are transmitted in the shield 104.

Here, in a case in which the X-ray output apparatus 100 controls the output of the parallel X-ray beams in the X-ray output unit 102 and the positions through which the parallel X-ray beams are transmitted in the shield 104 and in which the parallel X-ray beams are not transmitted simultaneously in the positions corresponding to adjacent regions in the shield 104, for example, X-rays radiated to the portions shown as X1 to X4 shown in FIG. 8, for example, are blocked by the shield 104 and are not radiated to the subject O. Further, for example, even in a case in which the parallel X-ray beams are partly allowed to be transmitted simultaneously in the positions corresponding to adjacent regions in the shield 104, it is possible to further reduce the amount of X-rays radiated on the portions shown as X1 to X4 shown in FIG. 8, for example. Accordingly, by the X-ray output apparatus 100 controlling the output of the parallel X-ray beams in the X-ray output unit 102 and the positions through which the parallel X-ray beams are transmitted in the shield 104, it becomes possible to prevent the generation of the overlap radiation region (or to reduce the overlap radiation region) as shown in FIG. 4 in the subject O, and to reduce invalid radiation exposure in the subject O, for example.

Accordingly, the X-ray output apparatus 100 can reduce superfluous radiation exposure given to the subject.

Note that the configuration of the X-ray output apparatus according to the present embodiment is not restricted to the configuration shown in FIG. 16. For example, the X-ray output apparatus according to the present embodiment may further include a detection unit (not shown) having the same function and configuration as the detection apparatus 200 shown in FIG. 1.

Furthermore, the X-ray output apparatus according to the present embodiment is not necessarily configured by one device. For example, the X-ray output apparatus according to the present embodiment may be an X-ray output system configured by a plurality of apparatuses such as a "system configured by the control unit 106, the X-ray output unit 102, and/or the shield 104 each of which is a separate apparatus". In a case in which the X-ray output apparatus according to the present embodiment is configured by the plurality of apparatuses, the device having a role as the control unit 106 initiatively performs the processing according to the method of reducing radiation exposure according to the present embodiment to control an apparatus having a role as the X-ray output unit 102 and an apparatus having a role as the shield 104, thereby realizing the X-ray output system which can reduce superfluous radiation exposure given to the subject.

The X-ray output apparatus has been described as the present embodiment; however, the present embodiment shall not be restricted thereto. The present embodiment can be applied to various devices such as a CT (Computed Tomography) device (a device using omnidirectional projection data), an X-ray imaging device such as mammography, and a device having a tomosynthesis function (a device using the projection data in a limited angle direction, for example, less than 180 degrees).

(Program According to the Present Embodiment)

A program for causing a computer to function as the X-ray output apparatus according to the present embodiment (a program capable of performing the processing according to the method of reducing radiation exposure according to the present embodiment, such as a program for causing a computer to function as the control unit 106 shown in FIG. 16, for example) is executed in the computer so as to control the output of the parallel X-ray beams in the X-ray output unit, and the positions through which the parallel X-ray beams are transmitted in the shield. Accordingly, superfluous radiation exposure given to the subject can be reduced. Note that the X-ray output unit and the shield may be, for example, devices included in the computer or may be external devices of the computer.

Further, by a program for causing a computer to function as the X-ray output apparatus according to the present embodiment (a program capable of performing "processing for causing an apparatus that displays an image based on X-ray detection data of the parallel X-ray beams having been transmitted through the shield to perform display corresponding to the control of the output of the parallel X-ray beams and the positions through which the parallel X-ray beams are transmitted" in the control unit 106 shown in FIG. 16, for example) being executed in the computer, it is possible to increase the convenience of a user.

The preferred embodiments of the present disclosure have been described above with reference to the accompanying drawings, whilst the present disclosure is not limited to the above examples, of course. A person skilled in the art may find various alterations and modifications within the scope of the appended claims, and it should be understood that they will naturally come under the technical scope of the present disclosure.

For example, the program (computer program) for casing a computer to function as the X-ray output apparatus according to the present embodiment has been provided, a recoding medium having the program recorded thereon can also be provided.

The above configurations show examples of the present embodiment, and naturally belong to the technical scope of the present disclosure.

Additionally, the present technology may also be configured as below.

(1)

An X-ray output apparatus including:

an X-ray output unit including a plurality of X-ray sources and configured to output parallel X-ray beams;

a shield on which positions that are capable of blocking the output parallel X-ray beams and positions that are capable of transmitting the parallel X-ray beams are variable; and a control unit configured to control the output of the parallel X-ray beams in the X-ray output unit and the positions through which the parallel X-ray beams are transmitted in the shield.

(2)

The X-ray output apparatus according to (1), wherein, on the shield, grid-shaped regions are set, and wherein, in positions corresponding to adjacent regions among the regions on the shield, the control unit does not cause the parallel X-ray beams to be transmitted simultaneously.

(3)

The X-ray output apparatus according to (2), wherein the X-ray output unit includes a plurality of collimators that form the parallel X-ray beams, and wherein the regions on the shield correspond to the collimators in a one-to-one relation.

(4)

The X-ray output apparatus according to any one of (1) to (3), wherein the shield includes a transmission hole that causes the parallel X-ray beams to be transmitted, and wherein the control unit controls the position through which the X-rays are transmitted, by shifting a position of the transmission hole by moving the shield.

(5)

The X-ray output apparatus according to (4), wherein, in a case in which the shield is moved, the control unit causes the output of the parallel X-ray beams to be stopped in the X-ray output unit, and wherein, after the movement of the shield is completed, the control unit causes the X-ray output unit to output the parallel X-ray beams.

(6)

The X-ray output apparatus according to (4) or (5), wherein the transmission hole has a shape including at least a part that is not a straight line.

(7)

The X-ray output apparatus according to (6), wherein the shape of the transmission hole is an asymmetric shape.

(8)

The X-ray output apparatus according to (7), wherein the asymmetric shape is a shape in which, in a case in which a rectangular shape is used as a reference, asymmetry in a corner portion of the rectangular shape is smaller and asymmetry in a center portion of the rectangular shape is larger.

(9)

The X-ray output apparatus according to any one of (6) to (8), wherein the shape that is not a straight line in the transmission hole includes at least one of an arc shape, a convex and concave shape, and an uneven shape.

(10)

The X-ray output apparatus according to any one of (1) to (3), wherein, on the shield, grid-shaped regions are set, wherein the shield includes in each region a shield member opening-closing mechanism that causes the parallel X-ray beams to be selectively transmitted by opening and closing shield members, and wherein the control unit controls the positions through which the parallel X-ray beams are transmitted by setting each shield member opening-closing mechanism to be in a state in which the shield members are open or a state in which the shield members are closed.

(11)

The X-ray output apparatus according to (10), wherein the shape of the regions set on the shield includes at least a part that is not a straight line.

(12)

The X-ray output apparatus according to (11), wherein the shape of the regions is an asymmetric shape.

(13)

The X-ray output apparatus according to (11) or (12), wherein the shape of the part that is not a straight line includes at least one of an arc shape, a convex and concave shape, and an uneven shape.

(14)

The X-ray output apparatus according to any one of (10) to (13), wherein, in a case of changing the position of the shield member opening-closing mechanisms in a state in which the shield members are open in the shield, the control unit first sets all the shield member opening-closing mechanisms in the shield to be in a state in which the shield members are closed, and then sets a shield member opening-closing mechanism corresponding to a specific position in the shield to be in a state in which the shield members are open.

(15)

The X-ray output apparatus according to (14), wherein the control unit causes the X-ray output unit to keep outputting the parallel X-ray beams.

(16)

The X-ray output apparatus according to any one of (10) to (14), wherein, in a case of changing the position of the shield member opening-closing mechanisms in a state in which the shield members are open in the shield, the control unit causes the X-ray output unit to stop the output of the parallel X-ray beams until the change of the position of the shield member opening-closing mechanisms in a state in which the shield members are open is completed.

(17)

The X-ray output apparatus according to any one of (1) to (14) or (16), wherein the control unit causes the X-ray output unit to output the parallel X-ray beams only for a position corresponding to the positions through which the parallel X-ray beams are transmitted in the shield.

(18)

The X-ray output apparatus according to any one of (1) to (17), wherein the shield is provided in an output direction of the parallel X-ray beams in the X-ray output unit and between the X-ray output unit and a subject to which the parallel X-ray beams are radiated.

(19)

The X-ray output apparatus according to any one of (1) to (18), wherein the control unit causes an apparatus that displays an image to display an image corresponding to control of the output of the parallel X-ray beams and of the positions through which the parallel X-ray beams are transmitted, the image being based on X-ray detection data of the parallel X-ray beams that have been transmitted through the shield.

REFERENCE SIGNS LIST

100 X-ray output apparatus
102 X-ray output unit
104 shield
106 control unit
200 detection apparatus
1000 X-ray inspection system

The invention claimed is:
1. An X-ray output apparatus, comprising:
an X-ray output unit includes a plurality of X-ray sources and configured to output parallel X-ray beams;
a shield on which positions that block the output parallel X-ray beams and positions that transmit the parallel X-ray beams are variable; and
a control unit configured to:
control the output of the parallel X-ray beams in the X-ray output unit and the positions through which the parallel X-ray beams are transmitted in the shield.
2. The X-ray output apparatus according to claim 1, wherein, on the shield, grid-shaped regions are set, and
wherein the control unit is further configured to block concurrent transmission of the parallel X-ray beams in positions corresponding to adjacent regions among the grid-shaped regions on the shield.
3. The X-ray output apparatus according to claim 2, wherein the X-ray output unit further includes a plurality of collimators that form the parallel X-ray beams, and
wherein the grid-shaped regions on the shield correspond to the plurality of collimators in a one-to-one relation.
4. The X-ray output apparatus according to claim 1, wherein the shield includes a transmission hole to transmit the parallel X-ray beams, and
wherein the control unit is further configured to control the positions, through which the X-rays are transmitted, based on a movement of the shield to shift a position of the transmission hole.
5. The X-ray output apparatus according to claim 4, wherein, based on the movement of the shield, the control unit is further configured to control the X-ray output unit to stop the output of the parallel X-ray beams, and
wherein, upon completion of the movement of the shield, the control unit is further configured to control the X-ray output unit to output the parallel X-ray beams.
6. The X-ray output apparatus according to claim 4, wherein the transmission hole has a shape including at least a curved part.
7. The X-ray output apparatus according to claim 6, wherein the shape of the transmission hole is an asymmetric shape.
8. The X-ray output apparatus according to claim 7, wherein the asymmetric shape is a shape in which, based on a rectangular shape used as a reference, asymmetry in a corner portion of the rectangular shape is smaller than asymmetry in a center portion of the rectangular shape.
9. The X-ray output apparatus according to claim 6, wherein the shape in the transmission hole includes at least one of an arc shape, a convex shape, a concave shape, or an uneven shape.

10. The X-ray output apparatus according to claim 1, wherein, on the shield, grid-shaped regions are set,
wherein the shield includes, in each region of the grid-shaped regions, a shield member opening-closing mechanism to one of open or close shield members to selectively transmit the parallel X-ray beams
wherein the control unit is further configured to control the positions through which the parallel X-ray beams are transmitted, based on a state of the shield member opening-closing mechanism of each region of the grid-shaped regions, and
wherein the state comprises one of state in which the shield members are open or a state in which the shield members are closed.
11. The X-ray output apparatus according to claim 10, wherein a shape of the grid-shaped regions includes at least a curved part.
12. The X-ray output apparatus according to claim 11, wherein the shape of the grid-shaped regions is an asymmetric shape.
13. The X-ray output apparatus according to claim 11, wherein the shape of the curved part includes at least one of an arc shape, a convex shape, a concave shape, or an uneven shape.
14. The X-ray output apparatus according to claim 10, wherein, based on a change in the positions through which the parallel X-ray beams are transmitted, the control unit is further configured to set all the shield member opening-closing mechanisms in the shield to a state in which the shield members are closed, and then set a shield member opening-closing mechanism corresponding to a specific position in the shield to a state in which the shield members are open.
15. The X-ray output apparatus according to claim 14, wherein the control unit is further configured to control the X-ray output unit to continuously output the parallel X-ray beams.
16. The X-ray output apparatus according to claim 10, wherein, based on a change in the positions through which the parallel X-ray beams are transmitted, the control unit is further configured to control the X-ray output unit to stop the output of the parallel X-ray beams until the change in the positions through which the parallel X-ray beams are transmitted is completed.
17. The X-ray output apparatus according to claim 1, wherein the control unit is further configured to control the X-ray output unit to output the parallel X-ray beams only for a position corresponding to the positions through which the parallel X-ray beams are transmitted in the shield.
18. The X-ray output apparatus according to claim 1, wherein the shield is in an output direction of the parallel X-ray beams in the X-ray output unit, and
wherein the shield is in between the X-ray output unit and a subject to which the parallel X-ray beams are radiated.
19. The X-ray output apparatus according to claim 1, wherein the control unit is further configured to control an apparatus to display an image corresponding to control of the output of the parallel X-ray beams and of the positions through which the parallel X-ray beams are transmitted, and
wherein the image is based on X-ray detection data of the parallel X-ray beams transmitted through the shield.

* * * * *